US012611668B2

(12) United States Patent　　　　(10) Patent No.:　US 12,611,668 B2
Yager et al.　　　　　　　　　　　(45) Date of Patent:　Apr. 28, 2026

(54) LONG-TERM DRY STORAGE OF ENZYME-BASED REAGENTS IN A POROUS MATRIX

(71) Applicant: University of Washington, Seattle, WA (US)

(72) Inventors: Paul Yager, Seattle, WA (US); Sujatha Kumar, Seattle, WA (US)

(73) Assignee: University of Washington, Seattle, WA (US)

( * ) Notice: Subject to any disclaimer, the term of this patent is extended or adjusted under 35 U.S.C. 154(b) by 649 days.

(21) Appl. No.: 18/000,163

(22) PCT Filed: Aug. 13, 2021

(86) PCT No.: PCT/US2021/045857
§ 371 (c)(1),
(2) Date: Nov. 29, 2022

(87) PCT Pub. No.: WO2022/040027
PCT Pub. Date: Feb. 24, 2022

(65) Prior Publication Data
US 2023/0201824 A1　　Jun. 29, 2023

Related U.S. Application Data

(60) Provisional application No. 63/066,687, filed on Aug. 17, 2020.

(51) Int. Cl.
*G01N 21/64* (2006.01)
*B01L 3/00* (2006.01)
(Continued)

(52) U.S. Cl.
CPC ........... *B01L 3/502715* (2013.01); *B01L 3/52* (2013.01); *C12Q 1/6844* (2013.01); *B01L 2300/069* (2013.01)

(58) Field of Classification Search
CPC ................. B01L 3/502715; B01L 3/52; B01L 2300/069; C12Q 1/6844
See application file for complete search history.

(56) References Cited

U.S. PATENT DOCUMENTS

| 7,524,456 | B1 * | 4/2009 | Buechler | ............... | B01L 3/5027 |
| | | | | | 422/412 |
| 2005/0048530 | A1 * | 3/2005 | Borns | ................... | C12Q 1/6844 |
| | | | | | 435/6.1 |

(Continued)

FOREIGN PATENT DOCUMENTS

| CN | 111254223 | A | * | 6/2020 | ........... | C12Q 1/6844 |
| EP | 1995330 | A1 | * | 11/2008 | ........... | C12Q 1/6827 |

(Continued)

OTHER PUBLICATIONS

Yager, P. et al., "Point-of-Care Diagnostics for Global Health," Annu. Rev. Biomed. Eng. 2008. 10:107-44; DOI:10.1146/annurev.bioeng.10.061807.160524.

(Continued)

*Primary Examiner* — Jennifer Wecker
*Assistant Examiner* — Oyeleye Alexander Alabi
(74) *Attorney, Agent, or Firm* — Christensen O'Connor Johnson Kindness, PLLC

(57) ABSTRACT

Fluidic device and methods of preparing a fibrous pad comprising dried reagents deposited thereon are described. In an embodiment, the fluidic devices comprise a fibrous pad; and a lyophilized reagent depot configured to support nucleic amplification of a target nucleic acid molecule to produce amplicons when dissolved, wherein the lyophilized reagent depot is disposed on the fibrous pad, the lyophilized reagent depot comprising: a nucleic acid amplification (Continued)

enzyme configured to perform a nucleic acid amplification reaction producing amplicons; and a lyophilization agent.

23 Claims, 27 Drawing Sheets

Specification includes a Sequence Listing.

(51) Int. Cl.

| | |
|---|---|
| *B82Y 5/00* | (2011.01) |
| *B82Y 30/00* | (2011.01) |
| *B82Y 40/00* | (2011.01) |
| *C07F 5/02* | (2006.01) |
| *C09B 57/00* | (2006.01) |
| *C09K 11/06* | (2006.01) |
| *C12Q 1/6844* | (2018.01) |
| *G01N 1/30* | (2006.01) |
| *G01N 15/10* | (2024.01) |
| *G01N 15/1404* | (2024.01) |
| *G01N 15/1409* | (2024.01) |
| *G01N 15/1429* | (2024.01) |
| *G01N 15/149* | (2024.01) |
| *G01N 27/626* | (2021.01) |
| *G01N 31/22* | (2006.01) |
| *G01N 33/483* | (2006.01) |
| *G01N 33/543* | (2006.01) |
| *G01N 33/58* | (2006.01) |
| *G01N 33/68* | (2006.01) |

(56) References Cited

U.S. PATENT DOCUMENTS

| | | | | |
|---|---|---|---|---|
| 2009/0092967 | A1* | 4/2009 | Yao | C12Q 1/6844 |
| | | | | 435/6.12 |
| 2012/0003646 | A1* | 1/2012 | Joo | C12Q 1/6816 |
| | | | | 435/287.2 |
| 2017/0023555 | A1* | 1/2017 | Ou | G01N 33/84 |
| 2018/0113125 | A1 | 4/2018 | Sheehan et al. | |
| 2018/0214873 | A1* | 8/2018 | DeVoe | C12Q 1/686 |
| 2018/0259521 | A1 | 9/2018 | Kamei et al. | |
| 2019/0250156 | A1 | 8/2019 | Kamei et al. | |
| 2020/0166473 | A1* | 5/2020 | Hatamian | G01N 33/54388 |
| 2020/0345000 | A1 | 11/2020 | Jones et al. | |
| 2021/0040534 | A1 | 2/2021 | Zhou et al. | |

FOREIGN PATENT DOCUMENTS

| | | | | |
|---|---|---|---|---|
| WO | WO-2019232504 A2 | * | 12/2019 | C12M 45/02 |
| WO | WO-2020047000 A1 | * | 3/2020 | B01L 9/527 |
| WO | 2020/123016 A2 | | 6/2020 | |
| WO | WO-2018111728 A1 | * | 6/2020 | B01L 3/527 |

OTHER PUBLICATIONS

Derda, R. et al., "Enabling the Development and Deployment of Next Generation Point-of-Care Diagnostics," PLoS Negl. Trop. Dis., May 14, 2015; DOI:10.1371/journal.pntd.0003676, pp. 1-16.

Mothershed, E.A. and A. M. Whitney, "Nucleic acid-based methods for the detection of bacterial pathogens: Present and future considerations for the clinical laboratory," Clin. Chim. Acta 363 (2006) 206-220.

Ince, J. and A. McNally, "Development of rapid, automated diagnostics for infectious disease: advances and challenges," Expert Rev. Med. Devices (vol. 6, Issue 6), Nov. 2009, 11 pages.

Mahony, J.B., "Detection of Respiratory Viruses by Molecular Methods," Clin. Microbiol. Rev., vol. 21, No. 4, Oct. 2008; pp. 716-747.

Pipenburgm O. et al., "DNA Detection Using Recombination Proteins," PLoS Biol 4(7): e204, Jul. 2004; DOI: 10.1371/journal.pbio.0040204; pp. 1115-1121.

Walker, G. Terrance et al., "Strand displacement amplification—an isothermal, in vitro DNA amplification technique," Nucleic Acids Research, vol. 20, No. 7; pp. 1691-1696.

Helb, D. et al., "Rapid Detection of *Mycobacterium tuberculosis* and Rifampin Resistance by Use of On-Demand, Near-Patient Technology," Journal of Clinical Microbiology, vol. 48, No. 1; Jan. 2010, pp. 229-237; doi:10.1128/JCM.01463-09.

Tanriverdi, S. et al., "A Rapid and Automated Sample-to-Result HIV Load Test for Near-Patient Application," Supplement Article, JID 2010:201 (Suppl 1); pp. S52-S58.

Ritchie, A.V et al., "Samba HIV Semiquantitative Test, a New Point-of-Care Viral-Load-Monitoring Assay for Resource-Limited Settings," Journal of Clinical Microbiology, Sep. 2014 vol. 52 No. 9; pp. 3377-3383; doi:10.1128/JCM.00593-14.

Douthwaite S.T. et al., "Performance of a Novel Point-of-Care Molecular Assay for Detection of Influenza A and B Viruses and Respiratory Syncytial Virus (Enigma MiniLab) in Children with Acute Respiratory Infection," Journal of Clinical Microbiology, Jan. 2016 vol. 54 No. 1; pp. 212-215; doi: 10.1128/JCM.02887-15.

Niemz, A. et al., "Point-of-care nucleic acid testing for infectious diseases," Trends Biotechnol. May 2011 ; 29(5): 240-250. doi: 10.1016/j.tibtech.2011.01.007.

Asiello, P.J. and A.J. Baeumner, "Miniaturized isothermal nucleic acid amplification, a review," Lab Chip, 2011, 11, 1420-1430; DOI: 10.1039/c0lc00666a.

Mahalanabis, M. et al., "An integrated disposable device for DNA extraction and helicase dependent amplification," Biomed Microdevices (2010) 12:353-359; DOI 10.1007/s10544-009-9391-8.

Wang, C-H et al., "An integrated microfluidic loop-mediated-isothermal-amplification system for rapid sample pre-treatment and detection of viruses," Elsevier: Biosensors and Bioelectronics 26 (2011) 2045-2052.

Wang, Wang Wei, "Lyophilization and development of solid protein pharmaceuticals," Elsevier: International Journal of Pharmaceutics, 203:1-2 (2000); pp. 1-60.

Roskos, K. et al., "Simple System for Isothermal DNA Amplification Coupled to Lateral Flow Detection," PLOS One; Jul. 2013 | vol. 8 | Issue 7 | e69355; pp. 1-8.

Magro, L. et al., "Paper-based RNA detection and multiplexed analysis for Ebola virus diagnostics," Scientific Reports |7: 1347 | pp. 1-9; DOI:10.1038/s41598-017-00758-9.

Magro, L. et al., "Paper microfluidics for nucleic acid amplification testing (NAAT) of infectious diseases," Lab This Journal is © The Royal Society of Chemistry 2017; Lab Chip, 2017, 17, 2347-2371; DOI:10.1039/c7lc00013h.

Choi, J.R. et al., "An integrated paper-based sample-to-answer biosensor for nucleic acid testing at the point of care," This journal is © The Royal Society of Chemistry 2016, Lab Chip, 2016, 16, 611-621; DOI: 10.1039/c5lc01388g.

Rodriguez, N.M. et al., "A fully integrated paperfluidic molecular diagnostic chip for the extraction, amplification, and detection of nucleic acids from clinical samples," This journal is © The Royal Society of Chemistry 2016, Lab Chip, 2016, 16, 753-763; DOI: 10.1039/c5lc01392e.

Crowe, L.M. et al., "Is Trehalose Special for Preserving Dry Biomaterials?" Biophysical Journal vol. 71 Oct. 1996 2087-2093.

Mazzobre, M.F. et al., "Glass Transition and Thermal Stability of Lactase in Low-Moisture Amorphous Polymeric Matrices," Biotechnol. Prog. 1997, 13, 195-199.

Ohtake, S. and Y. John Wang, "Trehalose: Current Use and Future Applications," Journal of Pharmaceutical Sciences, vol. 100, No. 6, May 2011; pp. 2020-2053.

Lutz, S. et al., "Microfluidic lab-on-a-foil for nucleic acid analysis based on isothermal recombinase polymerase amplification (RPA)," This journal is ª The Royal Society of Chemistry 2010, Lab Chip, 2010, 10, 887-893; DOI: 10.1039/b921140c.

Al-Talib, H et al., "Rapid detection of methicillin-resistant *Staphylococcus aureus* by a newly developed dry reagent based poly-

(56)          References Cited

OTHER PUBLICATIONS merase chain reaction assay," Elsevier: SciVerse ScienceDirect; Journal of Microbiology, Immunology and Infection (2014) 47, 484e490.

Chua, A.L. et al., "Development of a dry reagent-based triplex PCR for the detection of toxigenic and non-toxigenic Vibrio cholerae," Journal of Medical Microbiology (2011), 60, 481-485; DOI 10.1099/jmm.0.027433-0.

Qu, S. et al., (2010) "Ambient Stable Quantitative PCR Reagents for the Detection of Yersinia pestis," PLoS Negl Trop Dis 4(3): e629. doi:10.1371/journal.pntd.0000629.

Bell. J. et al., "Multicenter clinical evaluation of the novel AlereTM i Influenza A&B isothermal nucleic acid amplification test," Elsevier: Journal of Clinical Virology 61(2014) 81-86.

Ang, G.Y. et al., "Development of a dry-reagent-based nucleic acid-sensing platform by coupling thermostabilised Late-PCR assay to an oligonucleotide-modified lateral flow biosensor," Elsevier. Journal of Microbiological Methods 118 (2015) 99-105.

Chander, Y. et al., "A novel thermostable polymerase for RNA and DNA loop-mediated isothermal amplification (LAMP)," frontiers in Microbiology; Aug. 2014 | vol. 5 | Article 395; pp. 1-11.

Hayashida, K. et al., "Direct detection of falciparum and nonfalciparum malaria DNA from a drop of blood with high sensitivity by the dried-LAMP system," Parasites & Vectors (2017) 10:26; pp. 1-9; DOI 10.1186/s13071-016-1949-8.

Shetty, P. et al., "Rapid amplification of *Mycobacterium tuberculosis* DNA on a paper substrate," This journal is © The Royal Society of Chemistry 2016 RSC Adv., 2016, 6, 56205-56212; DOI: 10.1039/c6ra07529k.

Phillips, E. A. et al., Microfluidic rapid and autonomous analytical device (microRAAD) to detect HIV from whole blood samples, This journal is © The Royal Society of Chemistry 2019, Lab Chip, 2019, 19, 3375-3386; DOI: 10.1039/c9lc00506d.

Tang, R. et al., "A fully disposable and integrated paper-based device for nucleic acid extraction, amplification and detection," Lab Chip, 2017, 17, 1270-1279; This journal is © The Royal Society of Chemistry 2017; DOI: 10.1039/c6lc01586g.

Ramachandran. S. et al., "Long-term dry storage of an enzyme-based reagent system for ELISA in point-of-care devices," Analyst, 2014, 139, 1456-1462; This Journal is © The Royal Society of Chemistry 2014; DOI: 10.1039/c3an02296j.

Fu, E. et al., "Two-Dimensional Paper Network Format That Enables Simple Multistep Assays for Use in Low Resource Settings in the Context of Malaria Antigen Detection," ACD Publications: Anal. Chem. 2012, 84, 4574-4579.

Toley, B. J. et al., "Isothermal strand displacement amplification (iSDA): a rapid and sensitive method of nucleic acid amplification for point-of-care diagnosis," Analyst, 2015, 140, 7540-7549; This Journal is 201 The Royal Society of Chemistry 2015; DOI: 10.1039/c5an01632k.

Lafleur, L. K. et al., "A rapid, instrument-free, sample-to-result nucleic acid amplification test," This Journal is © The Royal Society of Chemistry 2016, Lab Chip, 2016, 16, 3777-3787; DOI: 10.1039/c6lc00677a,.

Rasband, W. S., "Image processing and analysis in Java," Astrophysics Source Code Library, record ascl:1206.013; Jun. 2012 (Abstract).

Stevens, D. Y. et al., "Enabling a microfluidic immunoassay for the developing world by integration of on-card dry reagent storage," Lab Chip, 2008, 8, 2038-2045; This Journal is ª The Royal Society of Chemistry 2008; DOI: 10.1039/b811158h.

Lukhtanov, E. A. et al., "Novel DNA probes with low background and high hybridization-triggered fluorescence," Nucleic Acids Research, 2007, vol. 35, No. 5 e30; doi:10.1093/nar/gkl1136.

Nose, K. et al., Polyethylene Glycol Accelerates Loop-mediated Isothermal Amplification (LAMP) Reaction; The Pharmaceutical Society of Japan; 133(10) 1121-1126 (2013).

Sasahara, K. et al., "Effect of Dextran on Protein Stability and Conformation Attributed to Macromolecular Crowding," J. Mol. Biol. (2003) 326, 1227-1237; doi:10.1016/S0022-2836(02)01443-2.

Christiansen, A. et al., "Factors Defining Effects of Macromolecular Crowding on Protein Stability: an in vitro/in Silico Case Study using Cytochrome C," 2142-Pos Board B128; Biophys. J; Doi:10.1016/j.bpj.2010.12.2354.

Sun, W. Q. and P. Davidson, "Effect of Dextran Molecular Weight On Protein Stabilization During Freeze-Drying and Storage," CryoLetters 22, 285-292 (2001), 10 pages.

Mori, Y. et al., "Loop-mediated isothermalamplification(LAMP): recentprogress in researchanddevelopment," J Infect Chemother (2013) 19:404-411; DOI 10.1007/s10156-013-0590-0.

Kumar et al., "Long-term dry storage of enzyme-based reagents for isothermal nucleic acid amplification in a porous matrix for use in point-of-care diagnostic devices," Analyst, Oct. 26, 2020 (Oct. 26, 2020), vol. 145, No. 21. pp. 6875-6886.

International Preliminary Report on Patentability and Written Opinion mailed on Feb. 16, 2023, issued in Corresponding International Application No. PCT/US2021/045857, filed on Aug. 13, 2021, 7 pages.

International Search Report mailed on Dec. 16, 2021, issued in Corresponding International Application No. PCT/US2021/045857, filed on Aug. 13, 2021, 3 pages.

* cited by examiner

Trehalose + Dextran 70

Trehalose + PEG

Trehalose

Trehalose + Dextran 500

Trehalose + Dextran 70

Trehalose + PEG

*NEODYMIUM MAGNET (4 PLACES)*

*POROUS MATRIX WITH iSDA REAGENTS IN A 12-WELL PLATE*

*MAGNETS HOLD THE TWO PLATES TOGETHER*

*12-WELL PLATE IS PLACED OVER THE ALUMINUM PLATE*

*NEODYMIUM MAGNET (4 PLACES)*

*DRIED REAGENT DEPOT*

*DRIED REAGENT DEPOT*

*FIBROUS PAD*

*PUSH BUFFER*

LONG-TERM DRY STORAGE OF ENZYME-BASED REAGENTS IN A POROUS MATRIX

CROSS-REFERENCES TO RELATED APPLICATIONS

The present application is a National Stage application of International Application No. PCT/US2021/045857, filed on Aug. 13, 2021, entitled "LONG-TERM DRY STORAGE OF ENZYME-BASED REAGENTS IN A POROUS MATRIX," which claims the benefit of U.S. Provisional Patent Application No. 63/066,687, entitled, "LONG-TERM DRY STORAGE OF ENZYME-BASED REAGENTS FOR ISOTHERMAL NUCLEIC ACID AMPLIFICATION IN A POROUS MATRIX FOR USE IN POINT-OF-CARE DIAGNOSTIC DEVICES," filed Aug. 17, 2020, the contents of which are incorporated herein by reference in entirety.

STATEMENT OF GOVERNMENT LICENSE RIGHTS

This invention was made with Government support under Grant No. HR0011-11-2-0007 awarded by the Defense Advanced Research Projects Agency. The Government has certain rights in the invention.

STATEMENT REGARDING SEQUENCE LISTING

Applicant submits herewith a sequence listing in the form of an Annex C/ST.25 text file. The name of the text file is: 3915_P1139USPNPUW_Seq_List_ST25. The text file is 1 KB and was created on Sep. 22, 2021. The sequence listing submitted herewith does not go beyond the disclosure in the international application as filed.

BACKGROUND

Point-of-care (POC) devices that are accurate, robust, low cost, rapid, easy-to-use, equipment-free and disposable are in great demand for the diagnosis of diseases, especially in low-resource settings (LRS). However, the COVID-19 crisis has brought into sharp focus a great need to universally apply our tremendous gains in knowledge in molecular methods toward better POC diagnostics within the developed as well as developing worlds with high disease burden. Nucleic acid amplification tests (NAATs) are extremely sensitive methods for detecting DNA or RNA from pathogens and have relatively rapid turnaround times, such as getting results on the same day, compared to microbiological cultures or ELISA. Unfortunately, while NAATs aimed at POC for bacterial and viral infectious disease diagnosis have been developed, they are instrumented and expensive because they either require thermal cycling and/or complicated optics for fluorescence readout. Certain conventional NAATs aimed at POC provide dry storage of reagents in cartridges, are rapid, and have high sensitivity, but require trained users, need electricity, and are not affordable, limiting their use in low-resource settings.

There has been progress towards developing isothermal amplification systems in miniaturized microfluidic devices that are easy to use and suitable for LRS, but often at high prices and with varying levels of automation. A low-cost cartridge system with fluidic controls that executes isothermal amplification with lateral flow (LF) detection has recently been reported, but still requires a portable instrument. Paper fluidic devices have also been used for NAAT based testing as an inexpensive alternative to instrumented systems. All these systems, however, required fresh NAAT reagents to demonstrate the capability and did not address the dry storage of the reagents.

An important technical requirement for truly LRS-compatible NAAT-based POC systems is the ability to store dry reagents on the device. There are two main challenges. The first is the long-term stability of enzymes at elevated temperatures, especially for use in places where the ambient temperature could be as high as 45° C. The most promising approach is to store all reagents except simple buffers in dry form in a way that limits exposure to oxygen. The subsequent challenge is uniform rehydration of the reagents within the device to achieve optimal performance. Overcoming these challenges would circumvent the need for the "cold chain" or continuous refrigeration from the point of manufacture to the point of use, which is inconvenient in any diagnostic product, and may be too expensive and even unavailable in many LRS settings.

An autonomous device with a combination of isothermal amplification and paper fluidics for NAAT with dry reagents stable at elevated temperatures holds great promise for an inexpensive POC diagnosis, especially for LRS settings; however, such a device has not been developed prior to the work that went into the present disclosure.

SUMMARY

Toward that end, in an aspect, the present disclosure provides a fluidic device for performing nucleic acid amplification reactions on a sample. In an embodiment, the fluidic device comprises a fibrous pad; and a lyophilized reagent depot configured to support nucleic amplification of a target nucleic acid molecule, such as to produce amplicons when dissolved, wherein the lyophilized reagent depot is disposed on the fibrous pad, the lyophilized reagent depot comprising: a nucleic acid amplification enzyme configured to perform a nucleic acid amplification reaction producing amplicons; and a lyophilization agent.

In another aspect, the present disclosure provides a method of preparing a fibrous pad comprising dried reagents deposited thereon. In an embodiment, the method comprises depositing a reagent solution on a fibrous pad, the reagent solution comprising: a nucleic acid amplification enzyme configured to perform a nucleic acid amplification reaction producing amplicons; and a lyophilization agent; and lyophilizing the reagent solution to provide a lyophilized reagent depot on the fibrous pad.

In certain embodiments, the present disclosure provides a method for the long-term dry storage of the iSDA reagents, including probes with either a gold nanoparticle label for downstream lateral flow detection or a fluorescent probe for real-time detection in a porous matrix. The dry preservation of amplification reagents in a solid porous matrix could have high value for several applications with fluid connectivity especially in paper-based POC devices and applicable to low-resource settings, especially in hot climates where the ambient temperatures can be in the 40-45° C. range. The present disclosure also exemplifies this amplification method in an integrated 2-dimensional paper network (2DPN) sample-to-result device for methicillin resistant *Staphylococcus aureus* (MRSA) detection, the use of which is suitable to reduce the cost of diagnosis by eliminating the need for expensive instruments.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3A provides an example of images of lateral flow (LF) detection strips, according to an embodiment of the present disclosure, showing strong, medium, weak, and negative amplification signal for ldh1 iSDA with 100 genomic copies. FIGS. 3B and 3C show normalized intensities of LF test line and control line, respectively, according to embodiments of the present disclosure. Excellent stability was achieved for formulations that contained both trehalose and dextran (TD 70 and TD 500), and at all temperatures of storage as indicated by strong signal intensities for the test line and a weaker control line.

FIGS. 4A-4C illustrate real-time fluorescence of iSDA in Std 17 GF for the ldh1 target measured by plate-reader after rehydration in the porous matrix with different preservative formulations stored for 360 h, wherein FIG. 4A illustrates a reaction with fresh reagents, 4B illustrates a reaction with reagents stored at 22° C. and 4C with reagents stored at 45° C., according to embodiments of the present disclosure.

Curves are mean of 3 replicates, and error bars are standard deviation. The lift-off time of the reaction was within 15-18 minutes for all combinations of the preservatives. The peak fluorescence levels varied for different formulations with the highest signal for the formulation with trehalose and dextran. (T=10% trehalose, TP=10% trehalose+1% PEG, TD70=10% trehalose+2.5% dextran (~70 kDa), TD500=10% trehalose+2.5% dextran (500 kDa)).

Figures 1, 5A:
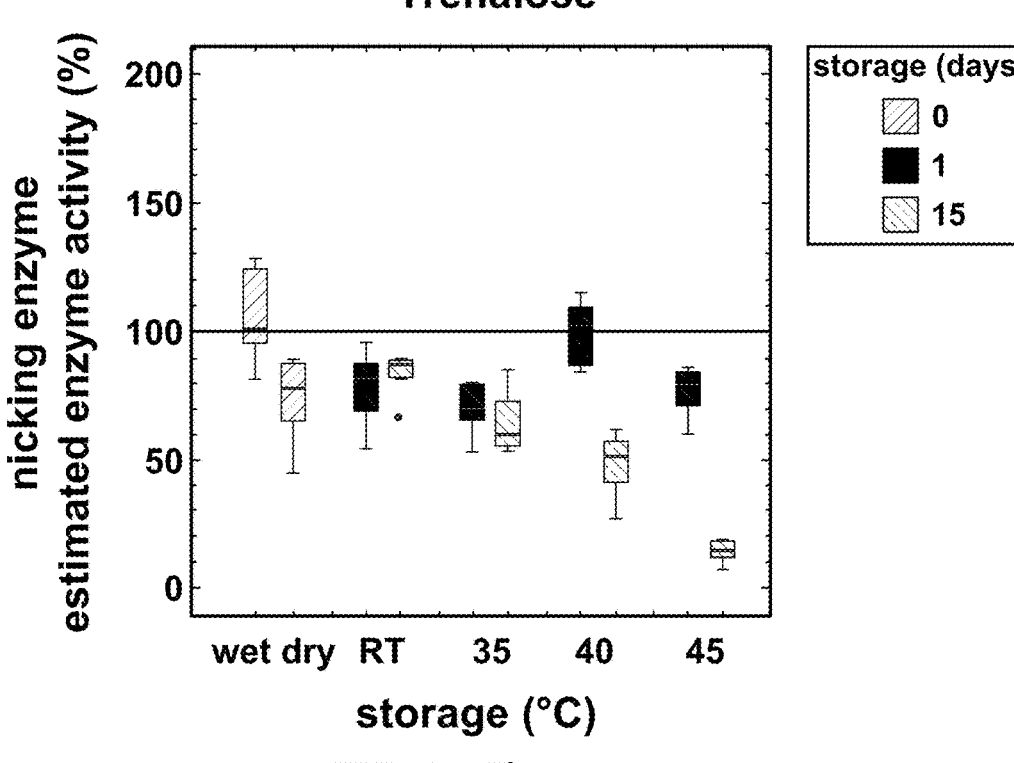
Figures 2, 5A:
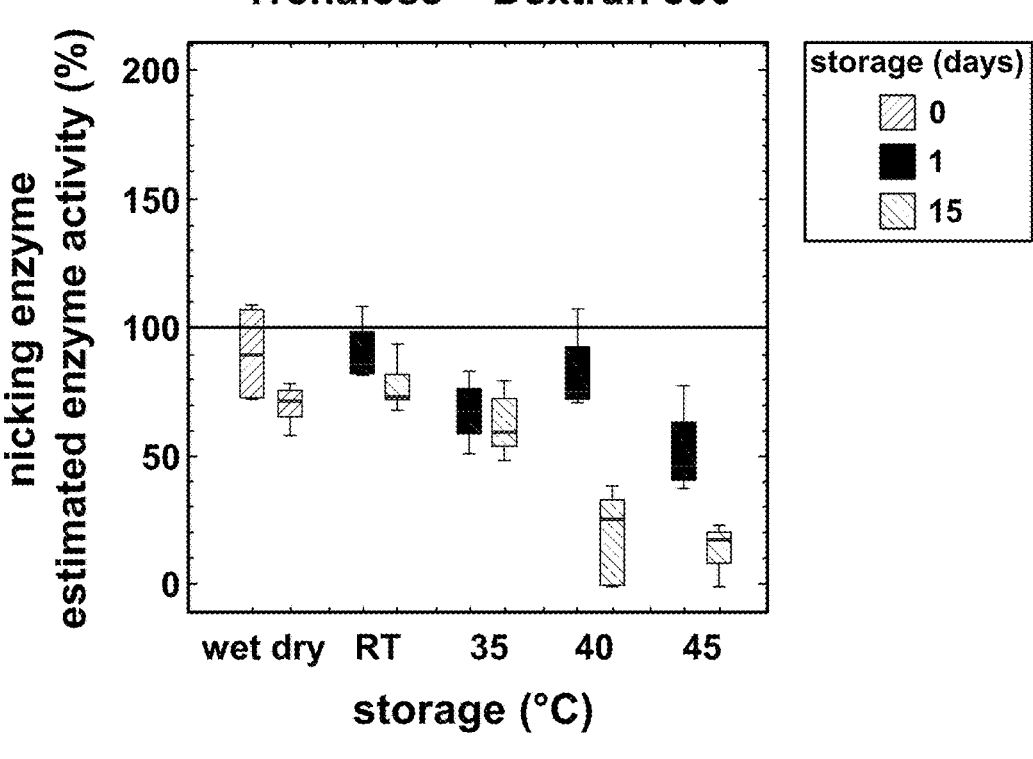
Figures 3, 5A:
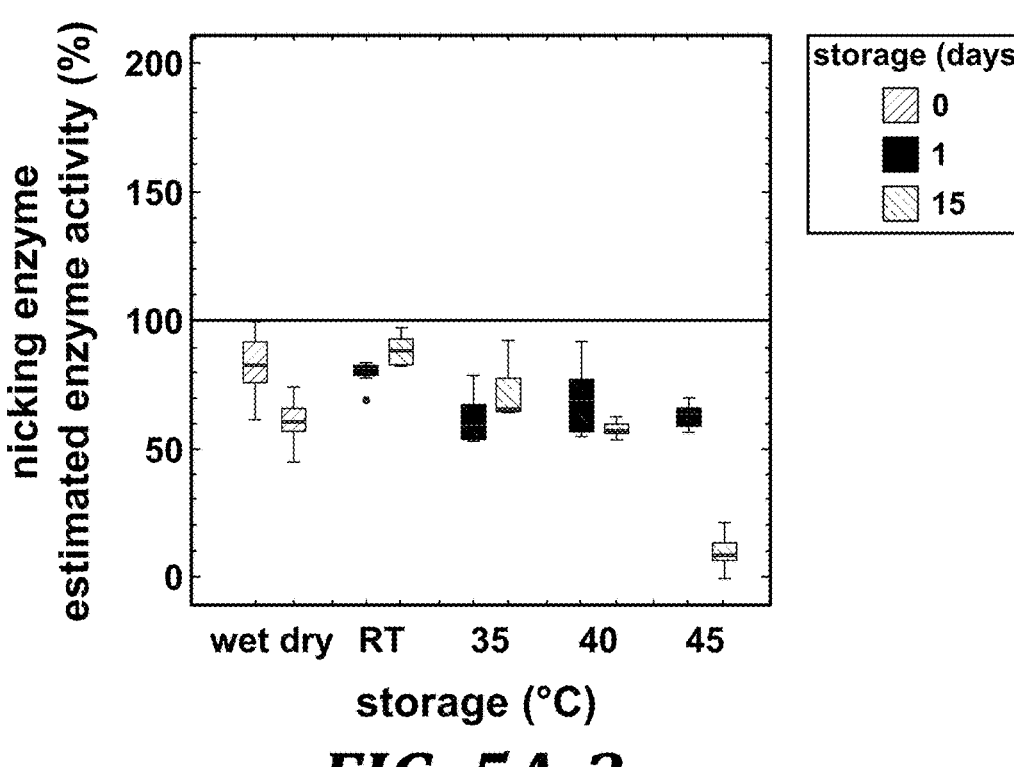
Figures 4, 5A:
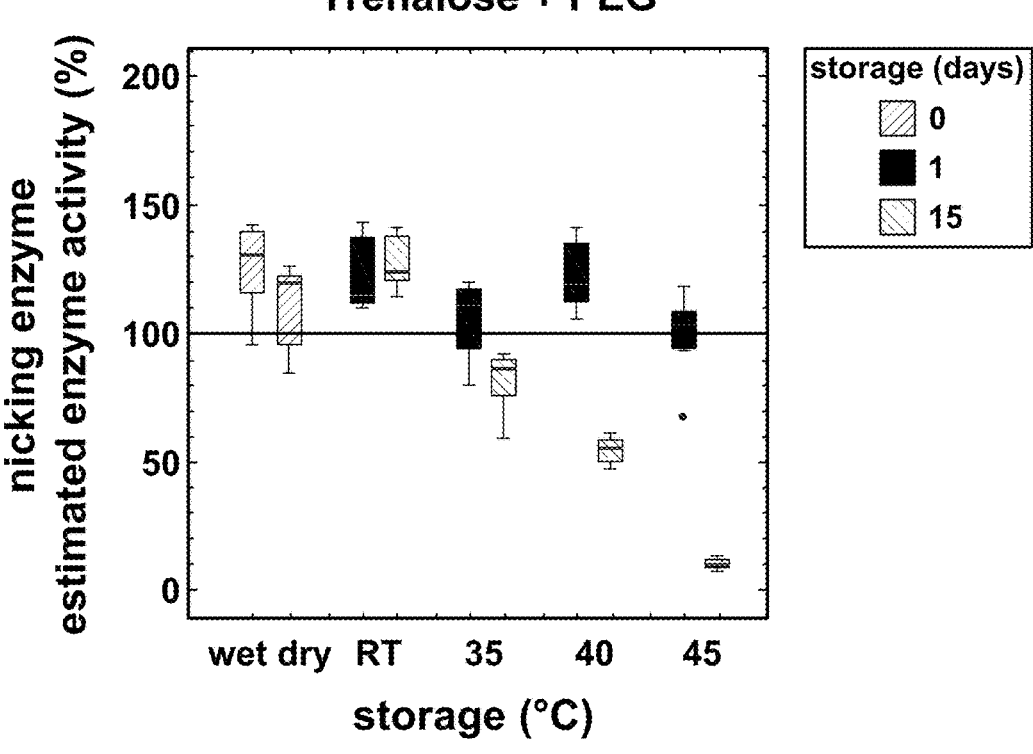
Figures 1, 5B:
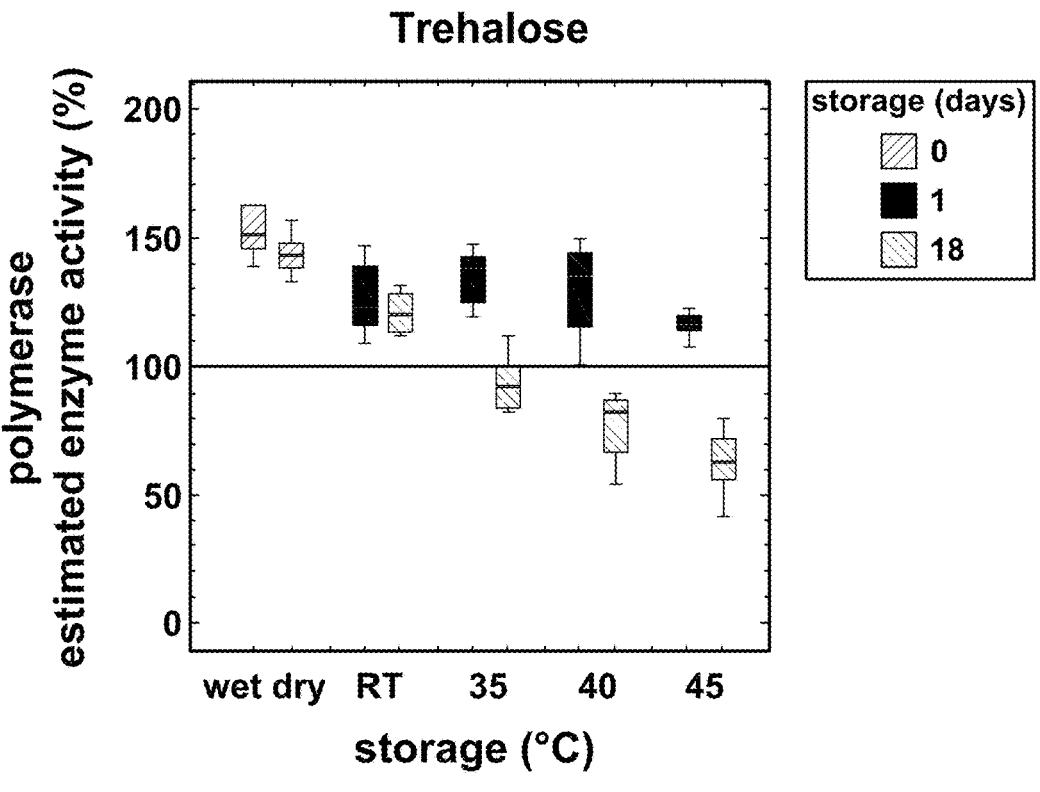
Figures 2, 5B:
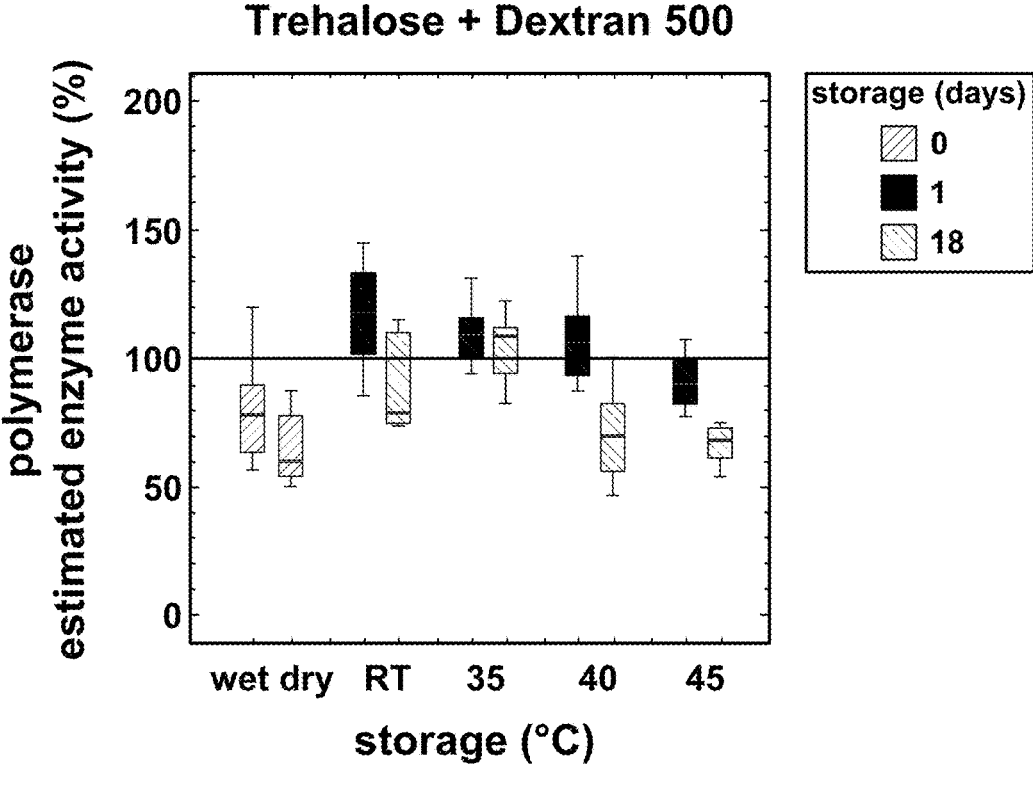
Figures 3, 5B:
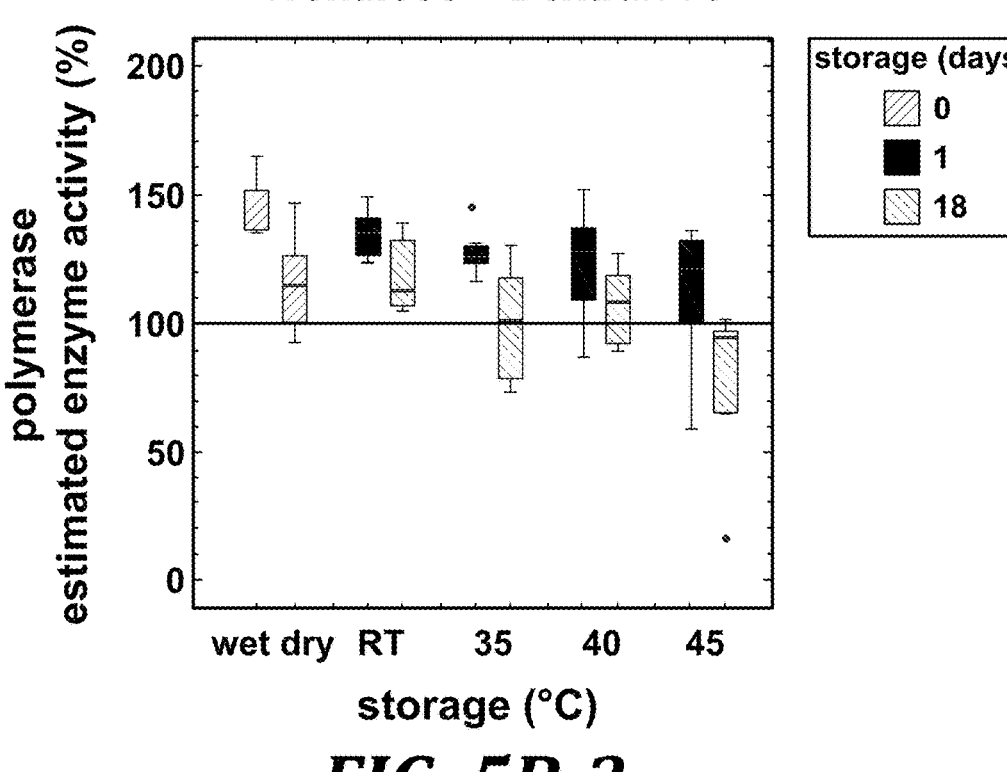
Figures 4, 5B:
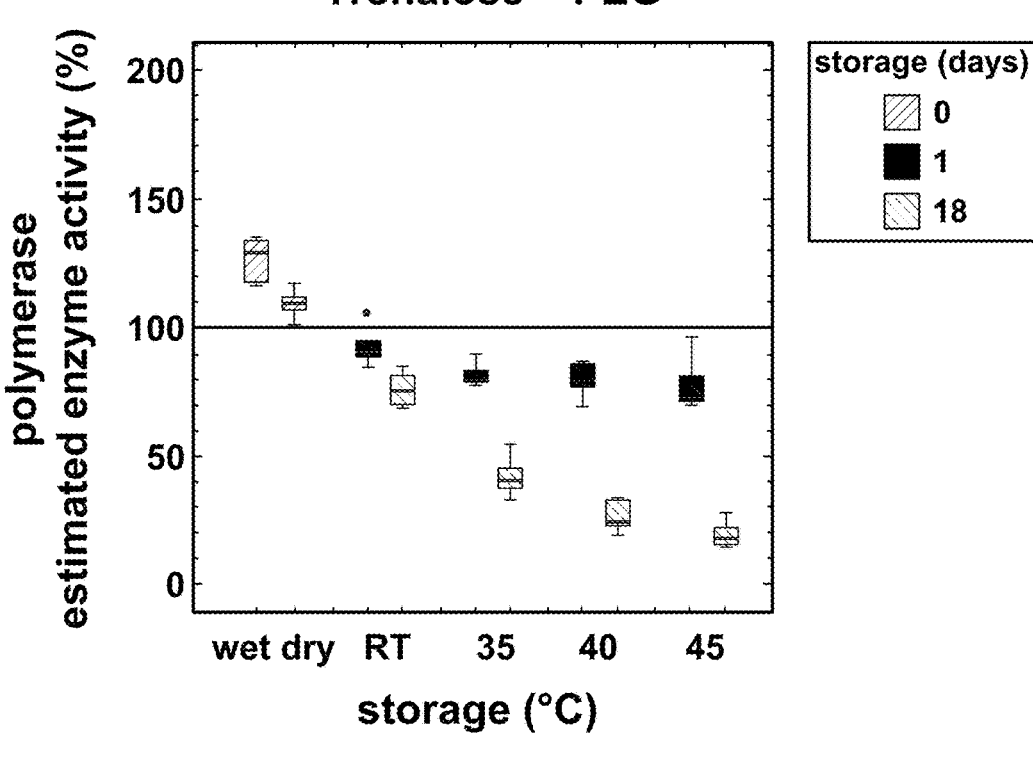

FIGS. 5A and 5B illustrate enzyme activity after dry storage in Std 17 GF with different preservation formulations (Table 1) and temperatures, according to embodiments of the present disclosure. The results are mean of 5 replicates, and error bars are standard deviation. FIG. 5A illustrates a nicking enzyme assay showing decreased activity at elevated temperatures of storage after 15 days, according to an embodiment of the present disclosure. FIG. 5B illustrates that polymerase activity does not appear to decrease appreciably over storage temperatures except for formulation with trehalose and PEG. PEG was overall detrimental to the storage of both the enzymes, according to an embodiment of the present disclosure.

Figure 6A:
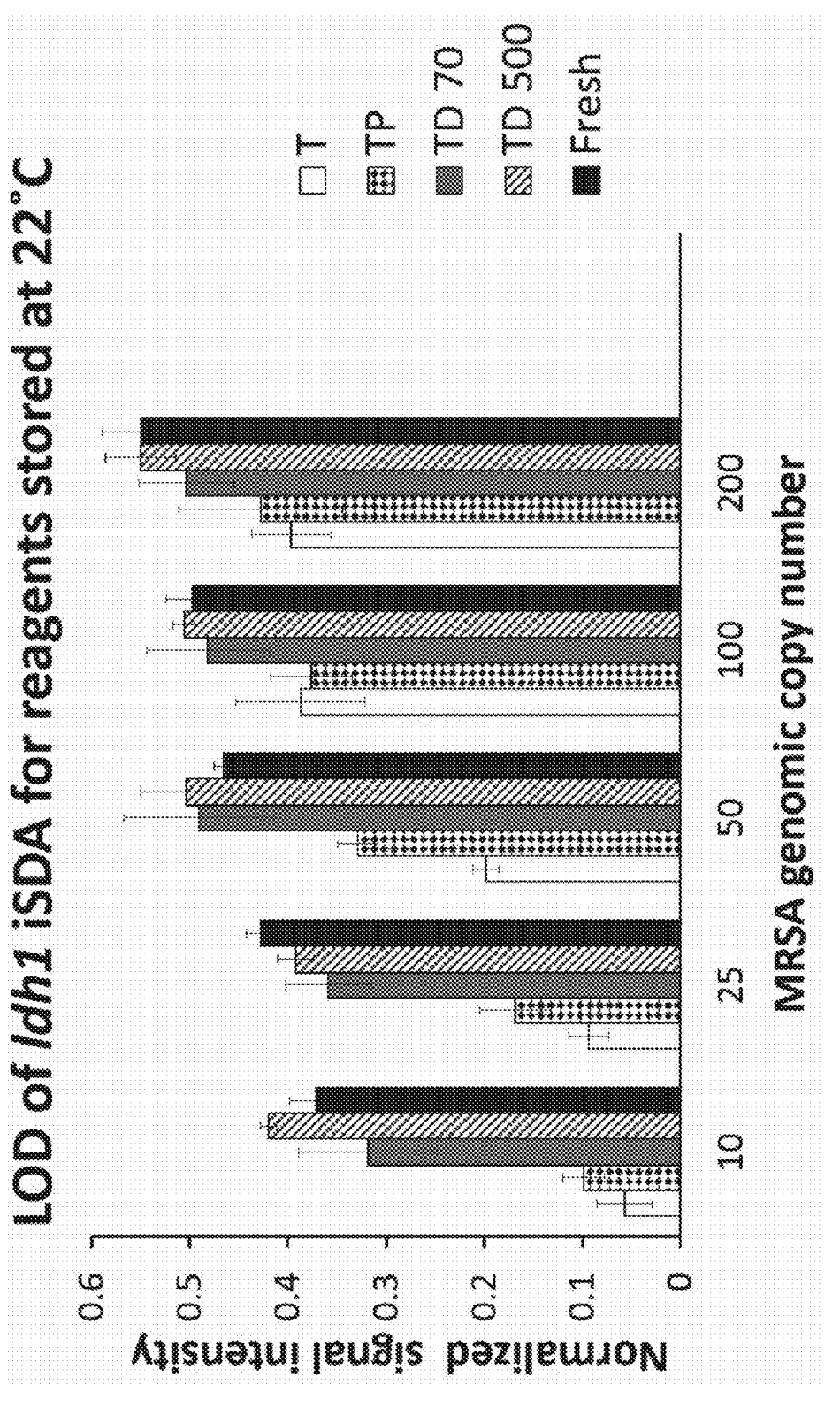
Figure 6B:
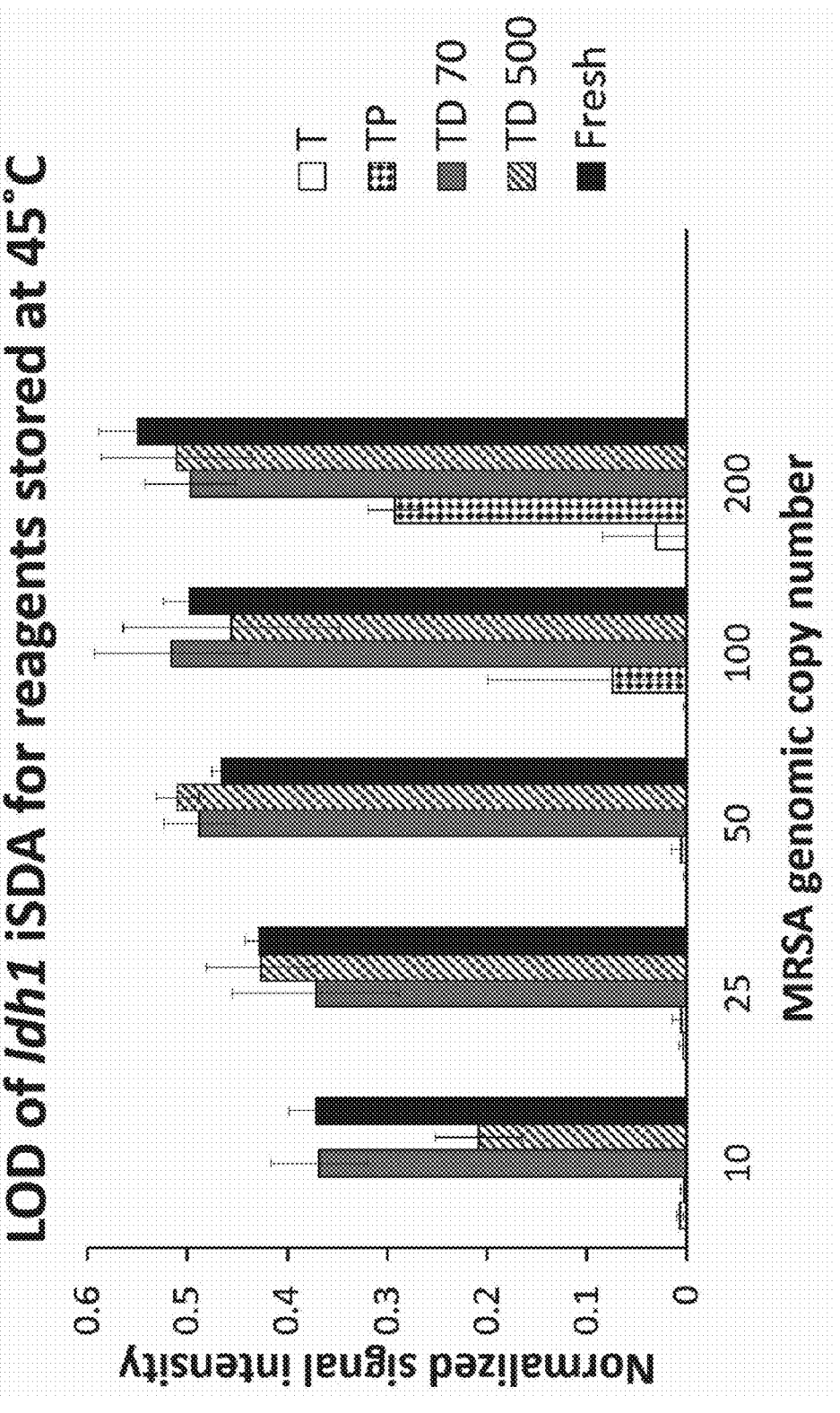

FIGS. 6A and 6B illustrate a limit of detection (LOD) of ldh1 iSDA with reagents stored dry in Std 17 GF at 22° C. and 45° C. for 360 h in different formulations of the preservatives, according to embodiments of the present disclosure. FIG. 6A shows normalized intensity of the lateral flow (LF) strip test line for samples stored at 22° C. Samples with trehalose and dextran (TD 70 & TD 500) in the iSDA mix showed excellent stability down to 10 genomic copies. FIG. 6B shows normalized intensity of the LF strip test line for samples stored at 45° C. Excellent stability down to 10 copies was achieved for samples with trehalose and dextran (TD 70 & TD 500), whereas samples with trehalose (T) only or trehalose and PEG (TP) showed poor stability.

Figure 7A:
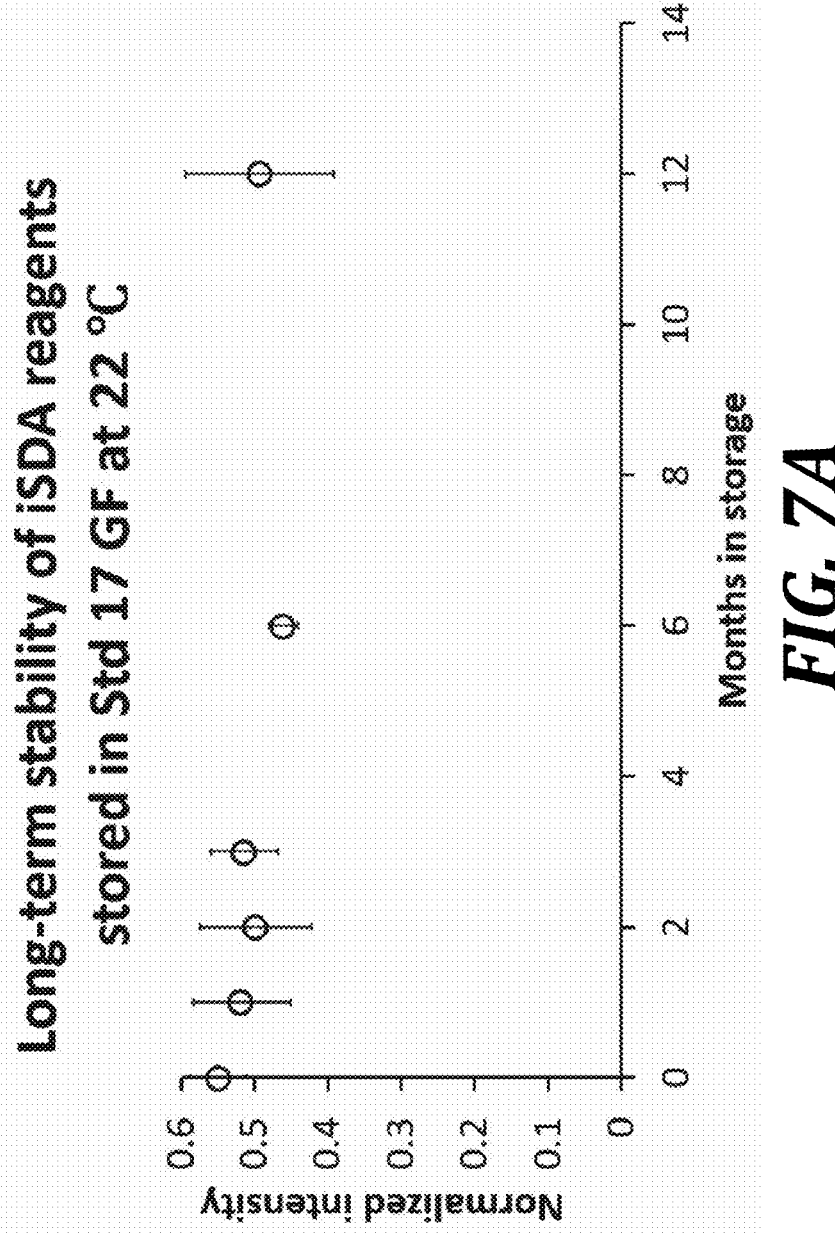
Figure 7B:
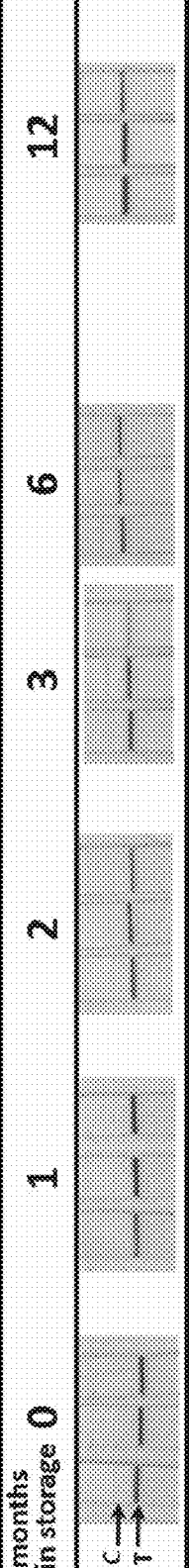
Figure 7C:
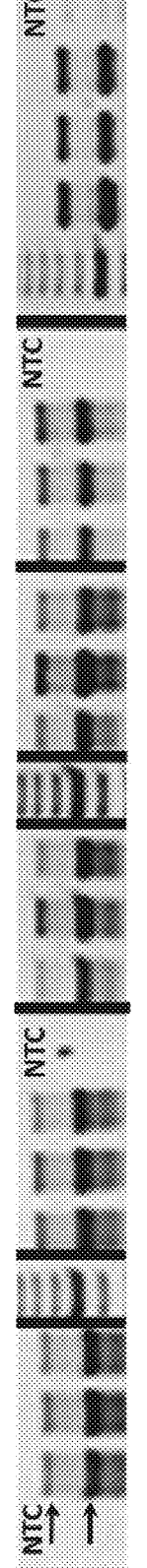

FIGS. 7A-7C demonstrate long-term iSDA reagent stability in the Std 17 GF, according to embodiments of the present disclosure. FIG. 7A illustrates normalized intensity of the LF test line after dry storage at 22° C. at different times. FIG. 7B includes images of lateral flow detection strips at various time points. "C" indicates the control line, and "T" is the test line for ldh1 assay on the detection strips. FIG. 7C includes corresponding gel images of the ldh1 amplicon products (indicated by arrow) at various time points. NTC is no template control. The iSDA reagents in the presence of 10% trehalose and 2.5% dextran performed well after 12 months of dry storage, with signal intensities similar to that observed with fresh reagents.

Figure 8A:
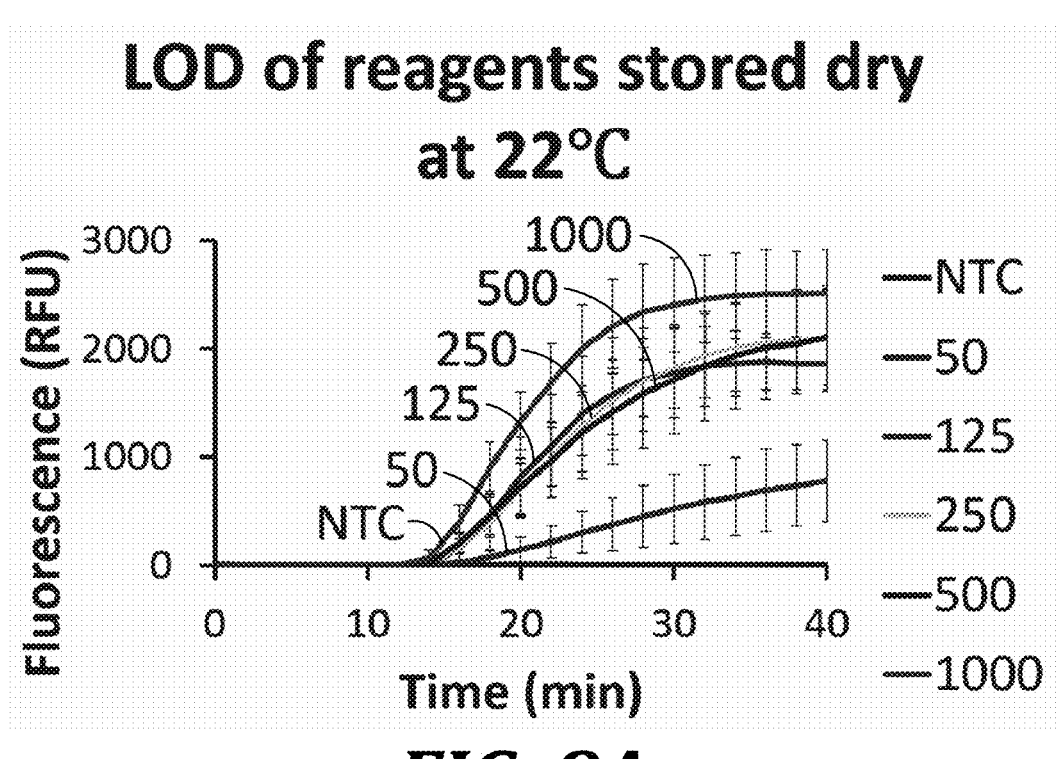

FIG. 8A is a calibration curve generated by varying the concentration of Au labels in Std 17 GF and quantified using a flat-bed scanner, in accordance with an embodiment of the present disclosure.

Figure 8B:
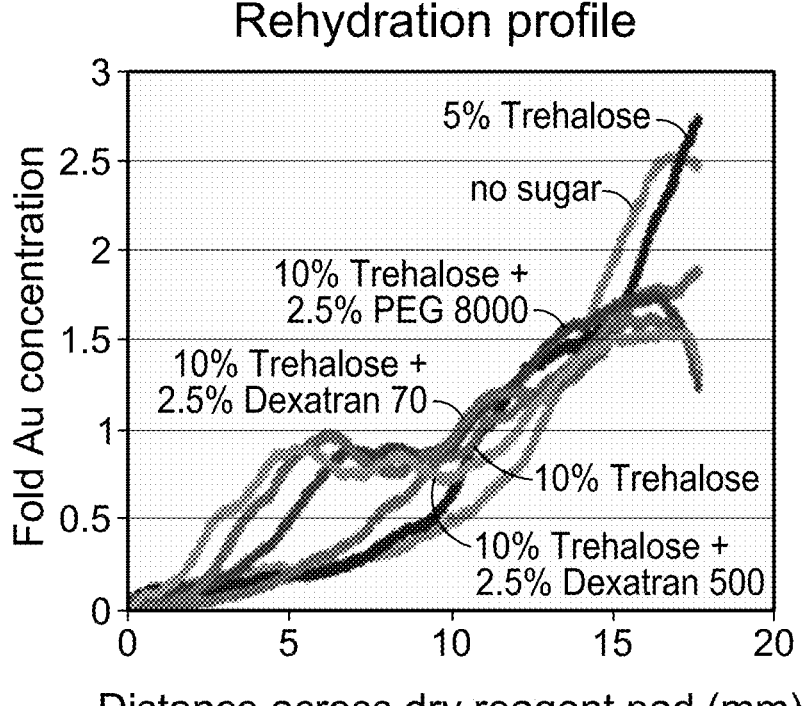

FIG. 8B illustrates average (N=3) intensity profiles of Au label visual marker across the length of the rehydrated reagent pads with different formulations, in accordance with an embodiment of the present disclosure. Pads with PEG or dextran had a more uniform distribution of the Au label compared to trehalose alone.

Figure 8C:
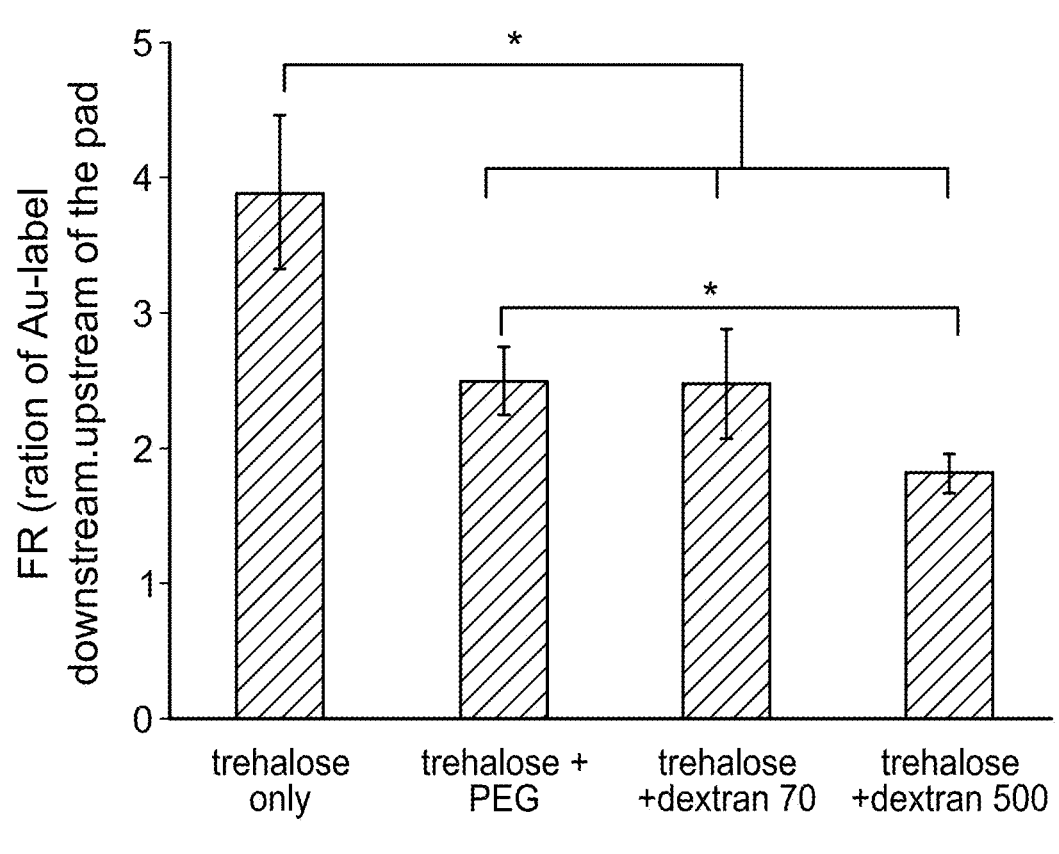

FIG. 8C illustrates a ratio "R" of Au label in the second half of the pad (downstream/upstream) with different formulations, in accordance with an embodiment of the present disclosure. A *P value >0 0.05 suggests that addition of PEG or dextran results in more uniform distribution of the reagents compared to trehalose alone.

Figure 8D:
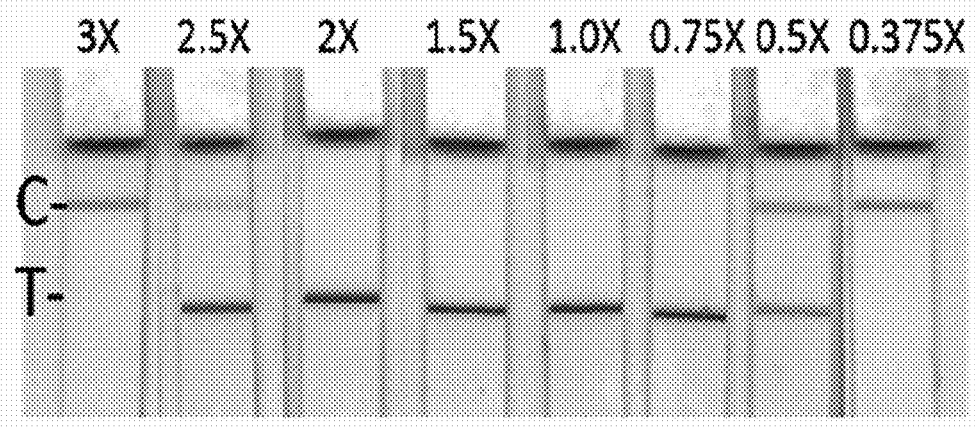

FIG. 8D provides lateral flow images of iSDA assay done with varying-fold concentration of reagents, in accordance with an embodiment of the present disclosure. The iSDA was tolerant to a wide range of fold-concentration of the reagents. Inhibition was seen at 3× and 0.375× fold concentration of the reagents. "C" indicates control line and "T" is test line for MRSA ldh1 assay on the detection strips.

Figure 9A:
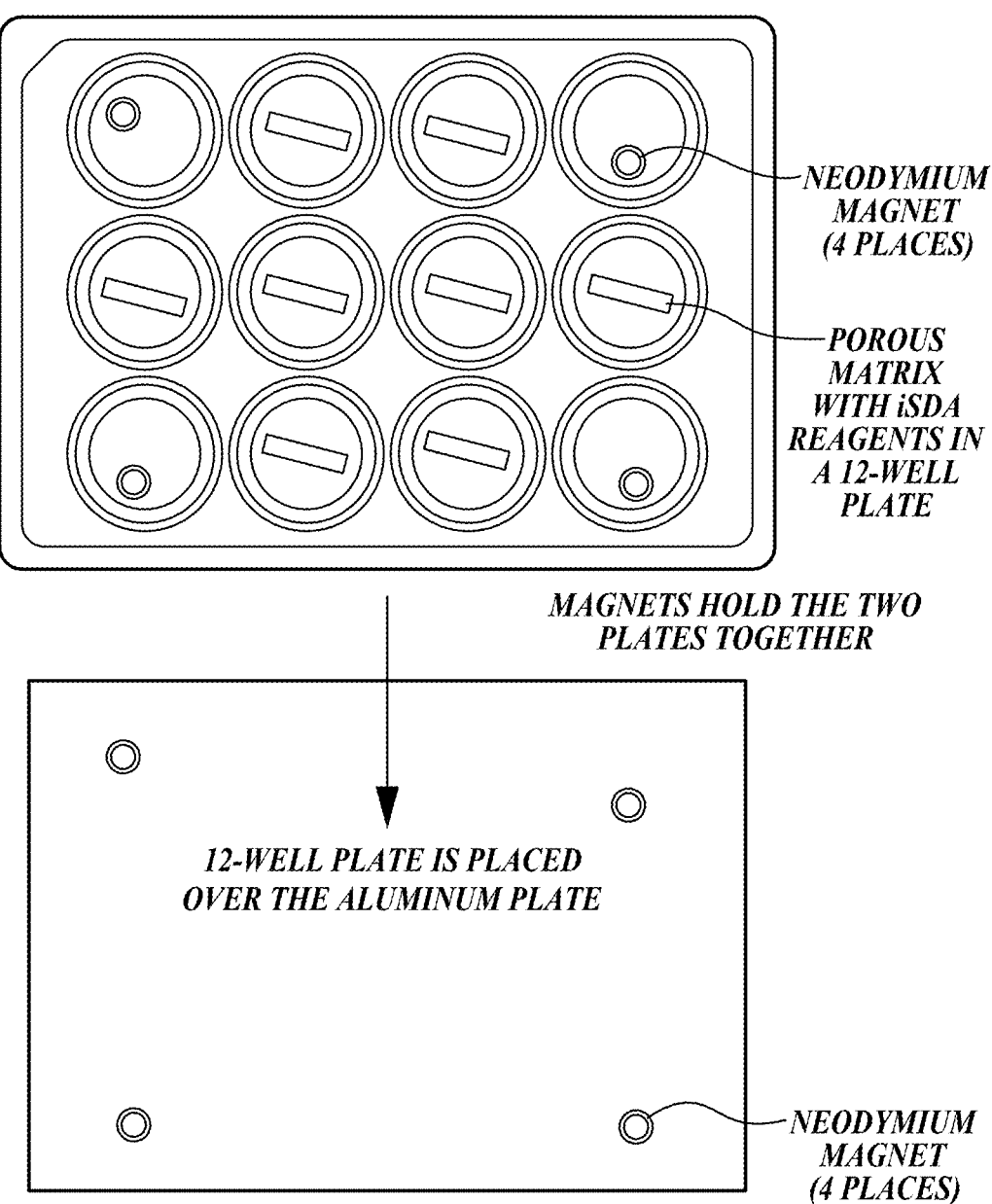
Figure 9B:
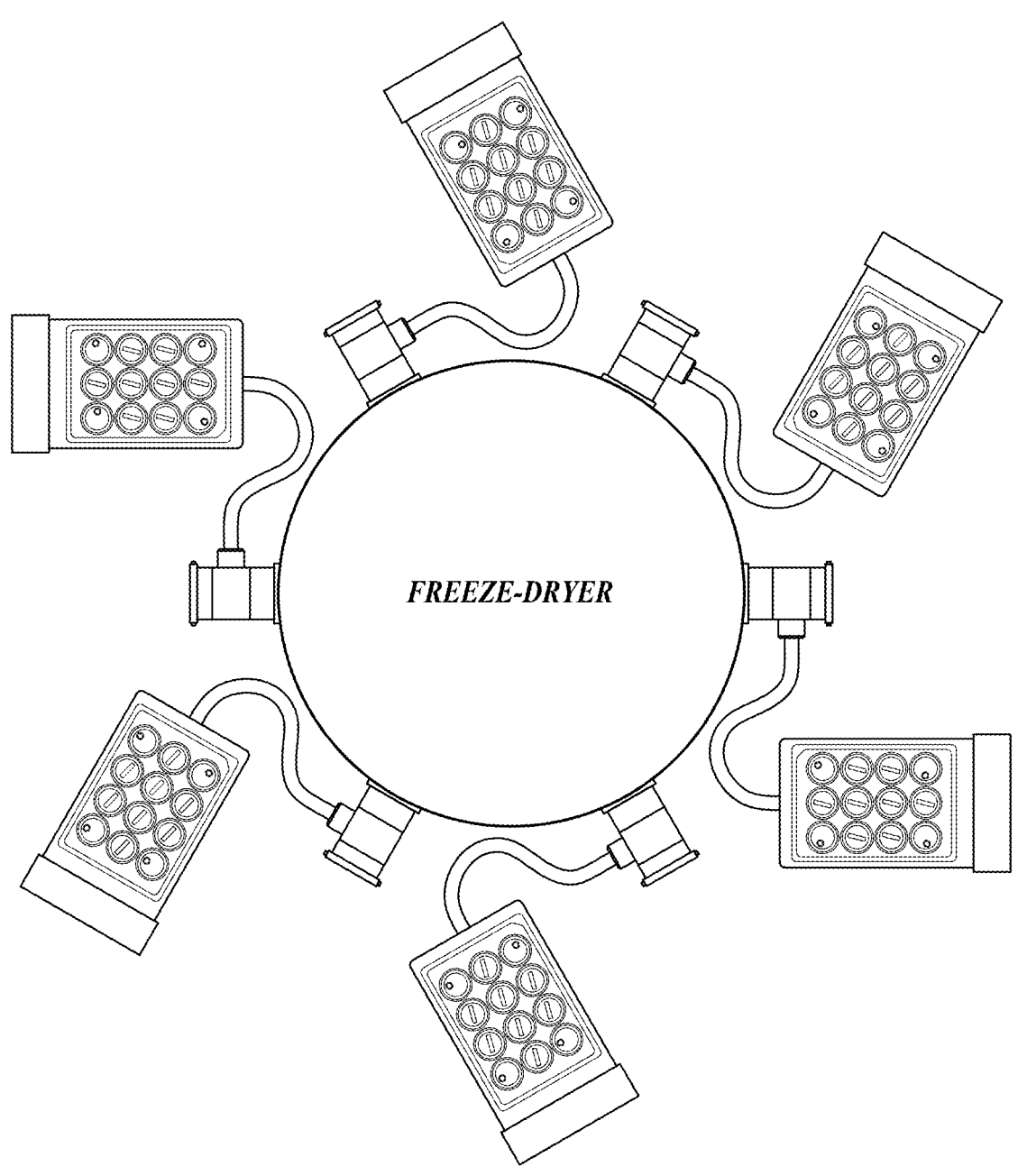
Figure 9C:
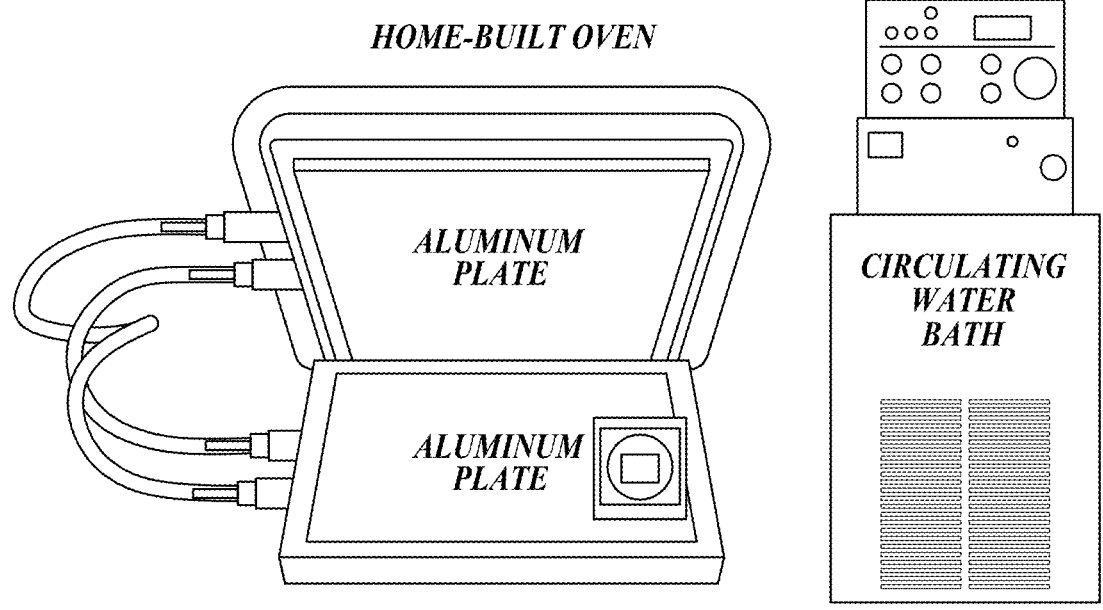

FIGS. 9A-9C illustrate an experimental setup for lyophilization, and amplification in a porous matrix, in accordance with embodiments of the present disclosure. FIG. 9A illustrates a 12-well plate containing iSDA reagent pads and magnets is placed over an aluminum (Al) plate with four magnets embedded in the corners, in accordance with embodiments of the present disclosure. The magnets hold the plates together during flash-freezing in liquid nitrogen. FIG. 9B illustrates a lyophilizer with well plates inside a fast-freeze flask, in accordance with embodiments of the present disclosure. FIG. 9C illustrates a custom-built oven for performing iSDA in the Secure-Seal hybridization chamber, in accordance with embodiments of the present disclosure.

Figure 10A:
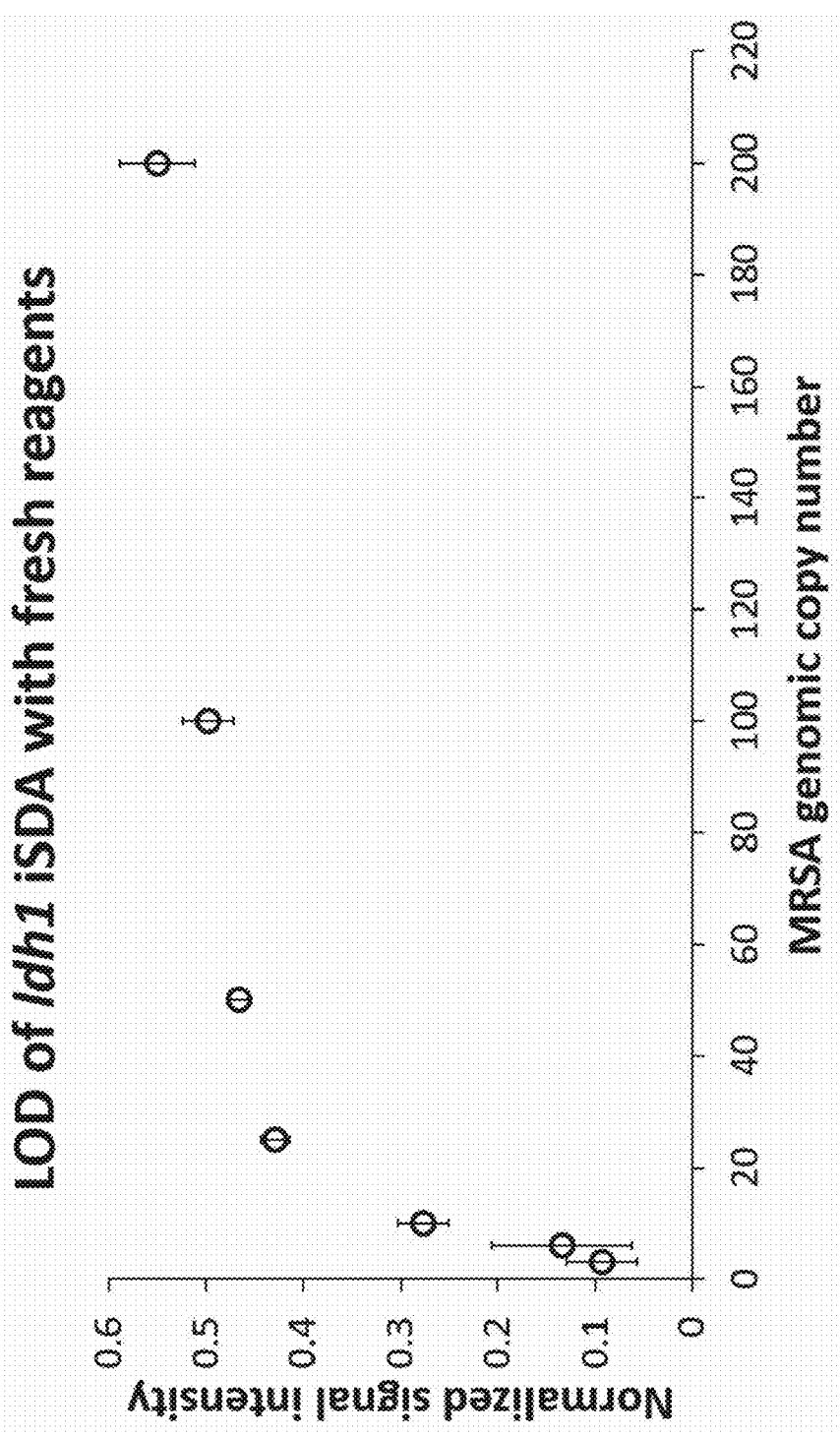
Figure 10B:
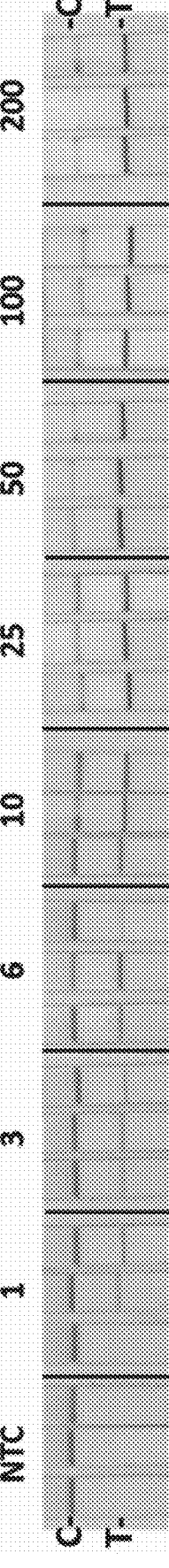

FIGS. 10A and 10B show a limit of detection (LOD) for ldh1 iSDA with fresh reagents in Std 17 GF, in accordance with an embodiment of the present disclosure. FIG. 10A is a chart showing signal intensities of the LF strips test line for a range of MRSA genomic copies and shown below. FIG. 10B provides corresponding LF strip images at varying genomic copy number. Note the signal intensities of control line increasing with decreasing copy number.

Figure 11A:
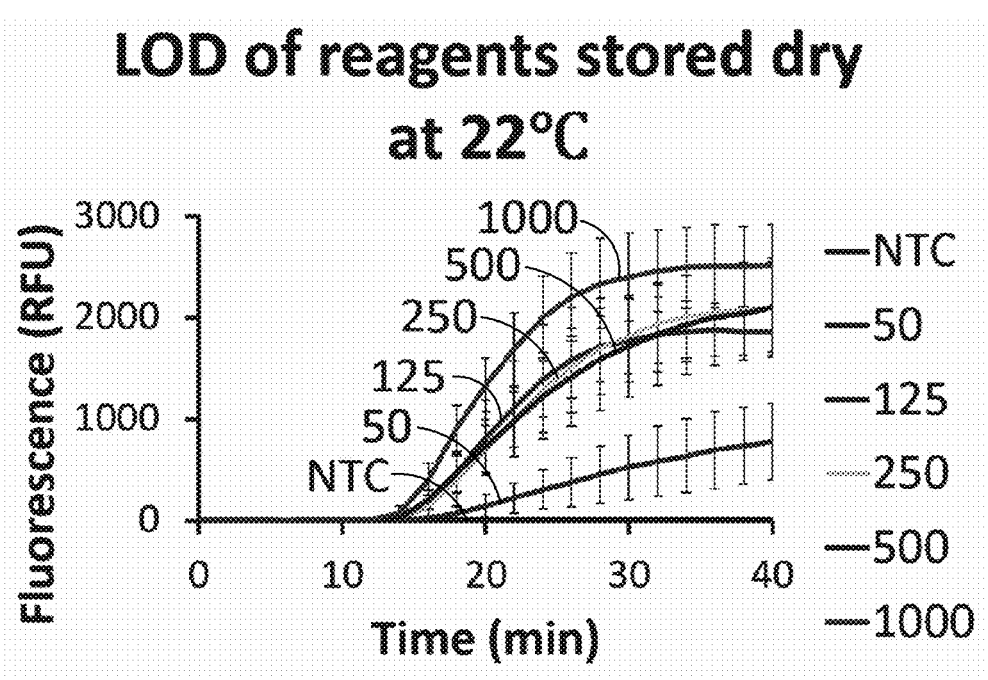
Figure 11B:
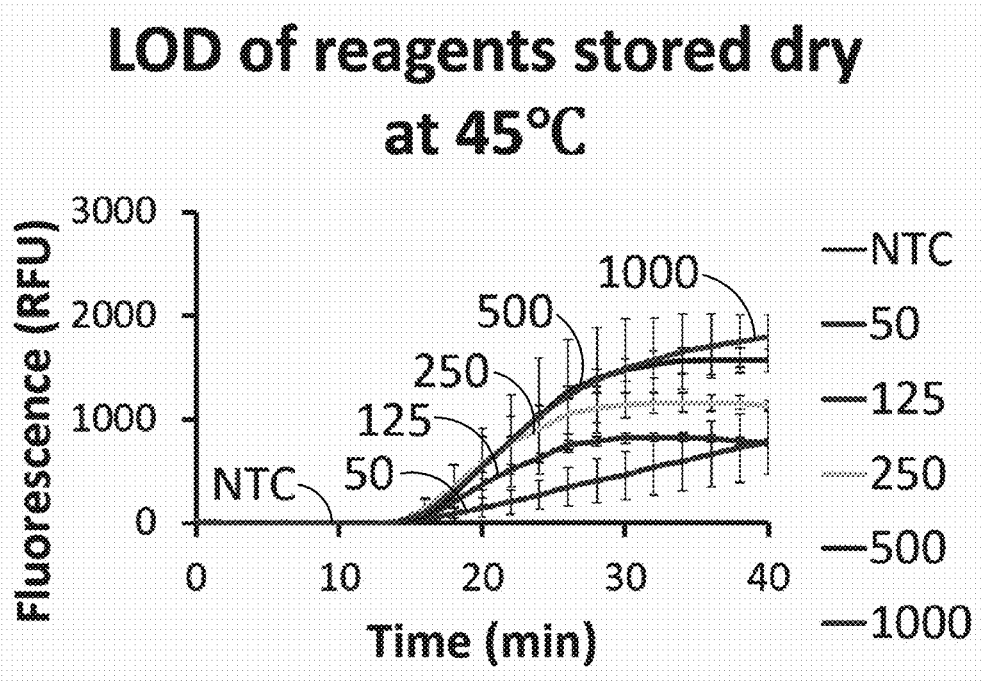

FIGS. 11A and 11B show an LOD of ldh1 iSDA with reagents stored in Std 17 GF for 360 h storage in the presence of trehalose and dextran (TD 500) measured by real-time fluorescence at (11A) 22° C. and (11B) 45° C., in accordance with an embodiment of the present disclosure. Curves are mean of 3 replicates, and error bars are standard deviation, in accordance with an embodiment of the present disclosure. The lift-off time for all copies was ~15 minutes; however, the peak fluorescence for 22° C. was higher than 45° C., indicating lower amplification efficiency at higher temperature storage.

Figure 12A:
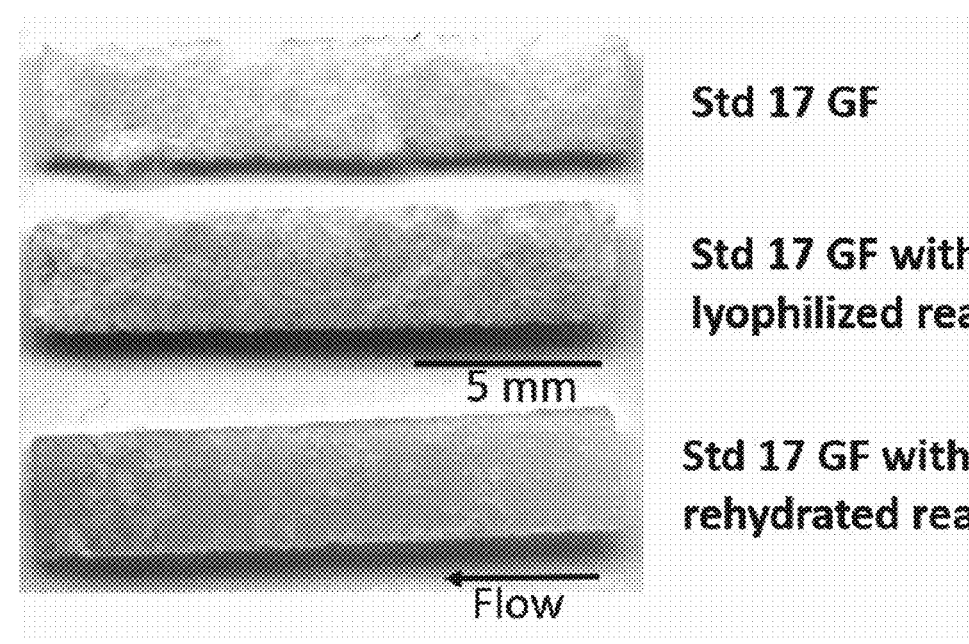

FIG. 12A provides flatbed scanned images of Std 17 GF, in accordance with an embodiment of the present disclosure, wherein lyophilized reagents in Std 17 GF appear uniform across the glass fiber pad and rehydrated pad shows reagent spread without excessive variation in reagent concentration as visualized by the Au label.

Figure 12B:
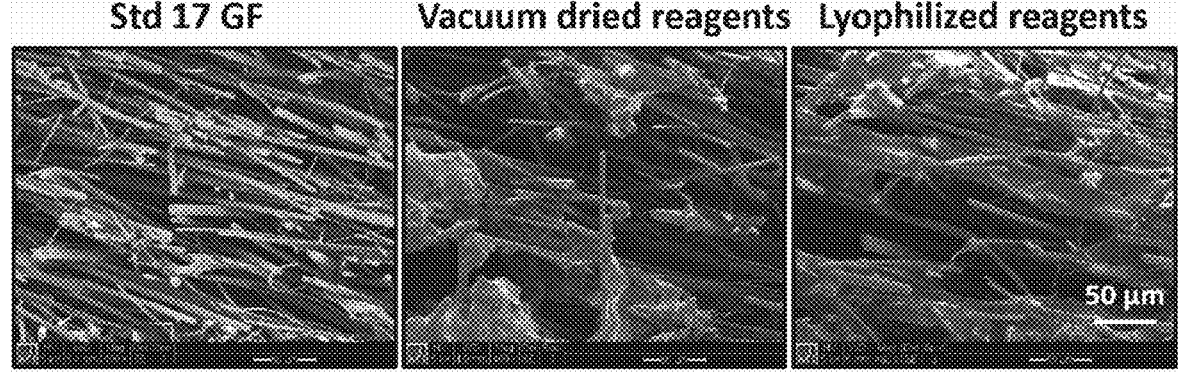

FIG. 12B provides scanning electron micrographs of Std 17 GF (scissor-cut cross-section) as received from the manufacturer, iSDA reagents in Std 17 GF dried by vacuum centrifugal evaporator and by lyophilization, in accordance with an embodiment of the present disclosure. Pore features in Std 17 GF are observable over a large length scale (~1-50 μm) with a range of fiber diameters. Reagents dried by vacuum appear as large clumps and seem to have a low surface area to volume ratio. In the lyophilized sample, the reagents migrate to the small features and appear as dry sheets stretched across the void with high surface area to volume ratio compared to the vacuum-dried sample.

Figure 13:
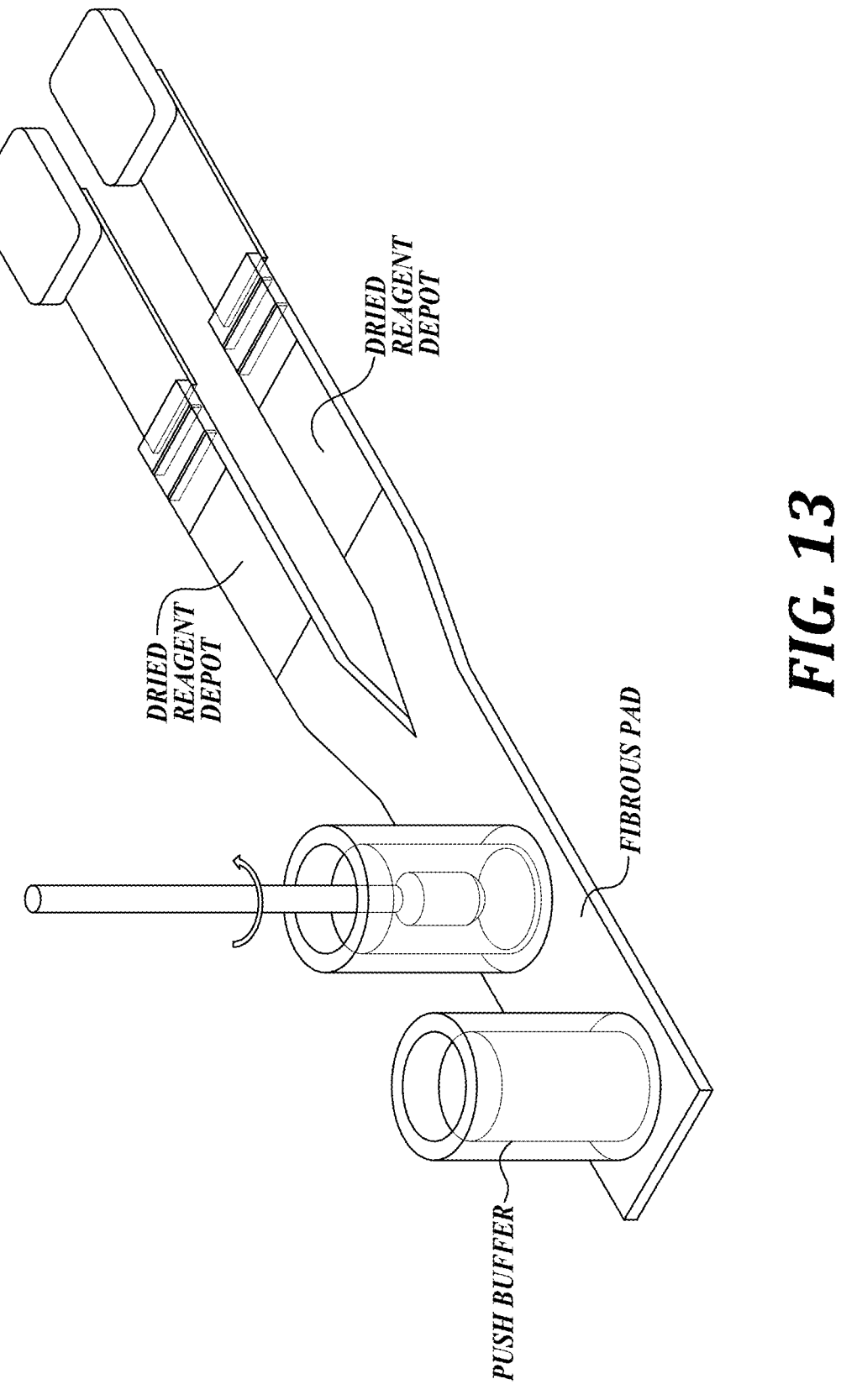

FIG. 13 is an isometric view of a fluidic device, in accordance with an embodiment of the present disclosure.

Figure 14:
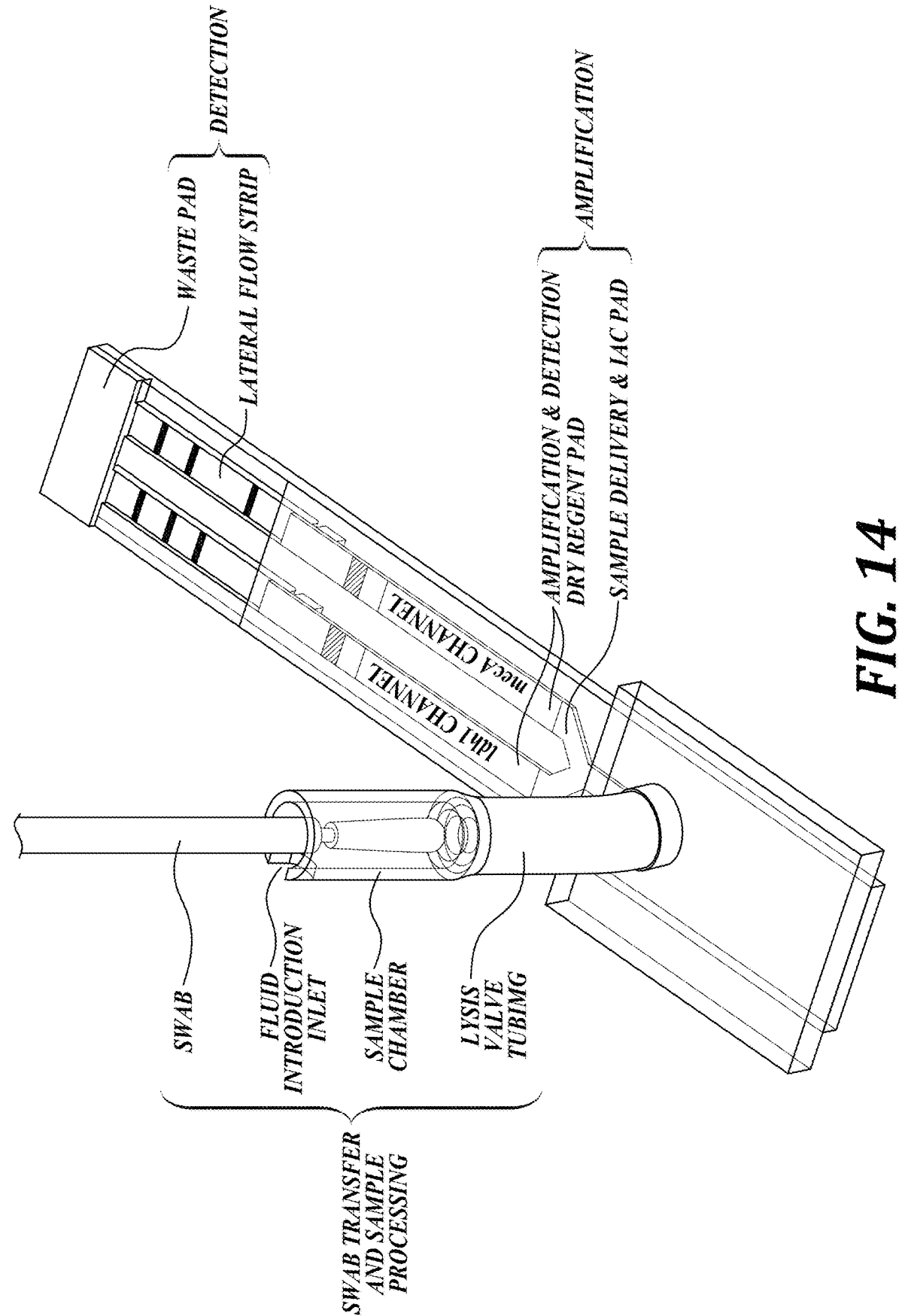

FIG. 14 is an isometric view of another fluidic device, in accordance with an embodiment of the present disclosure.

DETAILED DESCRIPTION

As noted further herein, use of nucleic acid amplification test (NAAT)-based point-of-care (POC) devices in low-resource settings is growing rapidly. However, key challenges include the ability to store the enzyme-based reagents in dry form in the device and the long-term stability of those reagents at elevated temperatures, especially where ambient temperatures could be as high as 45° C.

To address these and related challenges, the present disclosure is generally directed to fluidic devices including dried reagents disposed on or in a fibrous pad of the fluidic devices and methods of preparing a fibrous pad comprising dried reagents deposited thereon. As set forth in greater detail further herein, the fluidic devices of the present disclosure are suitable to provide a fluidic device comprising reagent suitable to support, for example, nucleic amplification of a target nucleic acid molecule to produce amplicons when dissolved, even after extended storage and/or shipping time periods. Further, such fluidic devices of the present disclosure are suitable to do so under elevated temperatures with little or no degradation in fluidic device performance in amplifying target nucleic acid molecules.

Fluidic Devices

In an aspect, the present disclosure provides a fluidic device for performing nucleic acid amplification reactions on a sample. In an embodiment, the fluidic device comprises a fibrous pad; and a lyophilized reagent depot configured to support nucleic amplification of a target nucleic acid molecule to produce amplicons when dissolved, the lyophilized reagent depot disposed on the fibrous pad, the lyophilized reagent depot comprising: a nucleic acid amplification enzyme configured to perform a nucleic acid amplification reaction producing amplicons; and a lyophilization agent.

As above, in an embodiment, the fluidic device of the present disclosure includes a fibrous pad. In an embodiment, the fibrous pad is porous membrane or other bibulous network configured to absorb a liquid into the fibrous pad and/or transport the liquid therethrough. As used herein, "fibrous pad," "porous element," or "porous membrane" refers to a porous membrane (e.g., a wick, pathway, leg, pad, delivery channel, etc.) through which fluid can travel by capillary action, such as paper, nitrocellulose, nylon, glass fiber, and the like. Unless the context clearly requires otherwise, a porous element can be two-dimensional or three-dimensional (when considering its height in addition to its length and width). Additionally, a porous membrane can be a single layer or may comprise two or more membranous layers. Although in some embodiments a specific term may be used (e.g., "wick," "pathway," "leg," "pad," "delivery channel," etc.), it should be understood that use of a different porous element is also within the scope of the present technology.

In an embodiment, the fibrous pad comprises a material selected from the group consisting of nitrocellulose, cellulose, quartz, glass fiber, and combinations thereof. In an embodiment, the fibrous pad comprises a material selected from the group consisting of nitrocellulose (FF80), cellulose (CF5), quartz (QMA), Fusion 5, MF1, 8964 glass fiber, Std 17 GF, and combinations thereof. In accordance with any embodiments of the present disclosure, the fibrous pad comprises Std 17 GF or MF1. In an embodiment, the fibrous pad comprises glass fiber. In an embodiment, the fibrous pad comprises a fibrous pad that has been washed of leachates before introducing the lyophilized reagent depot. As discussed in the Examples of the present disclosure, leachates of fibrous pads can, in certain embodiments, interfere with amplification of target nucleic acid molecules. By washing such leachates from the fibrous pads, nucleic acid amplification can occur, in certain embodiments, more efficiently and with a lower limit of detection.

In an embodiment, the fibrous pad is coated with or otherwise includes a blocking agent, such as a blocking agent suitable to prevent or mitigate non-specific binding of sample components, such as suitable to prevent or mitigate non-specific protein adhesion. In an embodiment the fibrous pad is coated with otherwise includes bovine serum albumin (BSA). In an embodiment, the fibrous pad is coated with or otherwise includes a surfactant. In an embodiment, the surfactant is a Tween surfactant, such as Tween 20.

The fluidic devices of the present disclosure include a reagent depot disposed on or in the fibrous pads. In an embodiment, the reagent depot includes one or more dried reagents disposed on or in the fibrous pad. In an embodiment, the reagent depot includes one or more lyophilized or freeze-dried reagents disposed on or in the fibrous pad. As discussed further herein, by lyophilizing or otherwise drying reagents of the reagent depot on or in the fibrous pad, the reactivity of the reagents is preserved or elongated in time. Without wishing to be bound by theory, it is believed that by lyophilizing or otherwise drying reagents of the reagent depot, the reagents of the reagent depot, including any nucleic acid amplification enzyme, have limited or reduced exposure to oxygen compared to an unlyophilized reagent. Such exposure to oxygen can reduce or degrade reagent reactivity.

In an embodiment, the reagent depot is configured to support nucleic acid amplification of a target nucleic acid molecule, such as to produce amplicons when dissolved, such as when dissolved in admixture with a sample containing the target nucleic acid molecule. The reagent depot can include reagents configured to support any type of nucleic acid amplification. In an embodiment, the reagent depot includes reagents configured to support a type of nucleic acid amplification selected from the group consisting of a polymerase chain reaction (PCR), reverse transcriptase PCR (RT-PCR), ligase chain reaction (LCR), loop mediated amplification (LAMP), reverse transcription loop mediated amplification (RT-LAMP), helicase dependent amplification (HDA), reverse transcription helicase dependent amplification (RT-HDA), recombinase polymerase amplification (RPA), reverse transcription recombinase polymerase amplification (RT-RPA), catalytic hairpin assembly reactions (CHA), hybridization chain reaction (HCR), entropy-driven catalysis, strand displacement amplification (SDA), and/or reverse transcription strand displacement amplification (RT-SDA). In an embodiment, the reagent depot includes reagents configured to support a type of nucleic acid amplification selected from the group consisting of nucleic acid sequence based amplification (NASBA), transcription mediated amplification (TMA), self-sustained sequence replication (3SR), and single primer isothermal amplification (SPIA). Other techniques that can be used include, e.g., signal mediated amplification of RNA technology (SMART), rolling circle amplification (RCA), hyper branched rolling circle amplification (HRCA), exponential amplification reaction (EXPAR), smart amplification (SmartAmp), isothermal and chimeric primer-initiated amplification of nucleic acids (ICANS), and multiple displacement amplification (MDA), isothermal strand displacement amplification (iSDA), or a combination thereof.

In an embodiment, the reagent depot includes reagents configured to support iSDA. In an embodiment, the reagent depot further comprises extension primers and bumper primers configured to amplify a target nucleic acid molecule, such as extension primers and bumper primers configured to amplify the target nucleic acid molecule through iSDA.

As above, in an embodiment, the lyophilization agent comprises one or more nucleic acid amplification enzyme configured to perform a nucleic acid amplification reaction producing amplicons. In an embodiment, the nucleic acid amplification enzyme is a polymerase. In an embodiment, the polymerase is WarmStart Bst 2.0 polymerase. In an embodiment, the lyophilized reagent depot further comprises a nicking enzyme. In an embodiment, the nicking enzyme is a Nt.BbvCI nicking enzyme. In an embodiment, the lyophilized reagent depot further comprises a reverse transcriptase.

As above, in an embodiment, the reagent depot comprises a lyophilization agent in addition to the nucleic acid amplification enzyme. Without wishing to be bound by theory, it is believed the lyophilization agent assists in lyophilizing reagents of the reagent depot, such as the nucleic acid amplification enzyme, such as by limiting exposure of such reagents to oxygen. Additionally, and without wishing to be bound by theory, it is believed that the lyophilization agent further assists in uniformly or more uniformly rehydrating the reagents of the reagent depot when contacted with a sample or other aqueous solution or suspension. In certain embodiments, without the lyophilization agent, reagents of the reagent depot rehydrate at a rate and/or at a concentration that is too high to effectively or efficiently participate in nucleic acid amplification reactions. Accordingly, in an embodiment, the lyophilization agent assists in slowing a rate at which reagents of the reagent depot dissolve into a fluid containing a sample. In this regard, in an embodiment, the lyophilization agent includes one or more reagents that are partially soluble in an aqueous solution, such as an aqueous sample.

In an embodiment, the lyophilization agent comprises a saccharide or a polyethylene oxide. In an embodiment, the lyophilization agent comprises trehalose, dextran, polyethylene glycol (PEG), and combinations thereof. In an embodiment, the lyophilization agent comprises trehalose and dextran. In an embodiment, the dextran has a weight average molecular weight of about 70 kDa. In accordance with any embodiments of the present disclosure, the dextran has a weight average molecular weight of about 500 kDa.

In an embodiment, the lyophilized reagent depot further comprises detection reagents configured selectively bind to a target, such as to hybridize with amplicons of a nucleic acid amplification reaction. In an embodiment, such detection reagents are also configured to emit or otherwise generate a detectable signal. Such a detectable signal can include emitting fluorescence such as in response to optical excitation. In an embodiment, the detectable agent is configured to change color in response to selectively binding to a target moiety. In an embodiment, the detection reagents comprise biotinylated detection probes configured to hybridize with the amplicons and streptavidin-coated gold nanoparticles. In accordance with any embodiments of the present disclosure, the detection reagents comprise a fluorophore, and wherein the fibrous pad further comprises a detection zone comprising a quencher configured to quench fluorescence of the fluorophore.

In an embodiment, the lyophilized reagent depot further comprises dNTPs. In an embodiment, the fluidic device further comprises a buffer or other liquid suitable to accept a sample, such as on a nasal swab, for application onto the fibrous pad and to dissolve the lyophilized reagent depot.

Examples of fluidic devices according to embodiments of the present disclosure are illustrated in FIGS. 13 and 14.

FIG. 13 is an isometric view of a fluidic device, in accordance with an embodiment of the present disclosure. As shown, the fluidic device includes sample receptacle shaped to receive a sample swab and positioned to contact the fibrous pad at a first position. In the illustrated embodiment, the sample receptacle is shown receiving a nasal swab.

The fluidic device is shown to further include a buffer depot containing a push buffer positioned upstream of the first position and configured to push the sample from the first position to a portion of the fibrous pad downstream of the first position.

Still referring to FIG. 13, the fluidic device is further shown to include a bifurcated portion of the fibrous pad comprising two portions each containing a dried reagent depot. In an embodiment, each dried reagent depot is according to any embodiment of the present disclosure. In an embodiment, one of the two portions contains reagents suitable to amplify a target nucleic acid molecule in or thought to be in the sample. In an embodiment, the other of the two portions contains reagents is suitable to amplify a second target nucleic acid in or thought to be in the sample or an internal amplification control in or thought to be in the sample. In an embodiment, the fibrous pad further includes detection reagent suitable to generate a detectable signal in response to contact with an amplicon of the target nucleic acid molecule and/or internal amplification control.

FIG. 14 is an isometric view of another fluidic device, in accordance with an embodiment of the present disclosure. As shown, the fluidic device includes a fluid introduction inlet and sample chamber shaped to receive a swab, such as a nasal swab containing a sample. The fluidic device is further shown to include a lysis valve tubing configured to selectively place the sample and/or the sample chamber in fluidic communication with a fibrous pad of the fluidic device.

Still referring to FIG. 14, the fibrous pad is shown to include a sample delivery and internal amplification control (IAC) portion shaped to deliver the sample from a portion of the fibrous pad adjacent to the lysis valve tubing to a portion of the fibrous pad on or in which a dried reagent depot is disposed. The dried reagent depot can be according to any embodiment of the present disclosure. As shown, one of the dry reagent pads is configured to amplify a mecA gene, and, in this regard, is configured to act as an internal amplification control. As also shown, the other dry reagent pad is configured to amplify an ldh1 gene, and, in this regard, is configured to amplify a target nucleic acid molecule in the sample.

As also shown in FIG. 14, the fibrous pad includes a lateral flow strip configured to produce a detectable signal in response to contact with a target nucleic acid molecule and/or an amplicon thereof.

Methods

In another aspect, the present disclosure provides a method of preparing a fibrous pad comprising dried reagents deposited thereon. In an embodiment, the method comprises depositing a reagent solution on a fibrous pad, the reagent solution comprising: a nucleic acid amplification enzyme configured to perform a nucleic acid amplification reaction producing amplicons; and a lyophilization agent; and lyophilizing the reagent solution to provide a lyophilized reagent depot on the fibrous pad.

In accordance with any embodiments of the present disclosure, the reagent solution comprises trehalose in a concentration of about 5% w/v to about 15% w/v and dextran in a concentration of about 1% w/v to about 5% w/v. In accordance with any embodiments of the present disclosure, the reagent solution comprises magnesium sulfate in a concentration of in a range of about 15 mM and about 150 mM. In accordance with any embodiments of the present disclosure, the reagent solution comprises potassium phosphate in a concentration of in a range of about 1 mM and about 15 mM.

In an embodiment, the lyophilization agent comprises trehalose, dextran, polyethylene glycol (PEG), and combinations thereof. In an embodiment, the lyophilization agent comprises trehalose and dextran.

In an embodiment, the fibrous pad comprises glass fiber.

In an embodiment, the method includes washing the fibrous pad to remove leachate from the fibrous pad before depositing the reagent solution on the fibrous pad. As discussed further herein, washing the leachate from the fibrous pad can increase amplification efficiency and reduce of limit of detection.

EXAMPLES

Isothermal Amplification in Porous Matrices

Porous matrices tested for iSDA compatibility included nitrocellulose FF80HP, cellulose CF5, Quartz QMA, Fusion 5, and Standard 17 Glass fiber (Std 17 GF). All these materials were purchased from GE Healthcare Life Sciences, Pittsburgh, PA Each material was cut to size with a hole-puncher to hold 25 µl of fluid when saturated. Reagents specific for detection of the *Staphylococcus aureus* ldh1 gene using iSDA contained 50 mM potassium phosphate buffer pH 7.6, 3.8 mM magnesium sulfate, 100 µM of each dNTP, 250 nM extension primer E1, 500 nM extension primer E2, 50 nM each of bumper primers B1 and B2, 8 units of WarmStart Bst 2.0 polymerase (New England Biolabs, Ipswich, MA) and 1.6 units of nicking enzyme Nt.BbvCI (New England Biolabs, Ipswich, MA). Primer and probe sequences for ldh1 amplification have been previously published.

To test the compatibility of the porous matrices, about 20 µl of iSDA reagent solution containing 100 copies of purified methicillin-resistant *S. aureus* (MRSA) genomic DNA (ATCC, BAA-1556) was added to the different porous matrices; the porous matrix was placed in a Secure-Seal hybridization chamber (Electron Microscopy Sciences, Hatfield, PA). DNA solutions were replaced with pure water for no-template controls (NTCs) for each of the materials tested. The samples were incubated in a custom electric oven at 49° C. for 30 min, which has been shown to be sufficient for amplification of even single copies of the target sequence using iSDA (although a custom oven was used, any device capable of holding 49° C. for 30 min could be substituted). After amplification, the pads were placed in a 0.2 ml tube with a hole at the bottom, which in turn was placed in a 0.5 ml tube, and centrifuged to collect the solution containing free amplicons. The amplicons were run on a gel electrophoresis system as described below.

Effect of Leachates from Porous Matrices on iSDA

The effect of possible inhibitors contained in the leachates from the different matrices (listed in the previous section) on iSDA was tested. The materials were first incubated in clean water at 49° C. for 30 minutes and then centrifuged in a 0.45 µM filter spin column. The extracted fluid was used as a replacement for water in the iSDA reaction. The reactions were carried out in a tube in a thermocycler (CFX96, Bio-Rad Laboratories, Hercules, CA) with 100 copies of the MRSA genomic DNA. The amplicons were run on a gel electrophoresis system, as described below.

Lyophilization and Long-Term Storage of iSDA and Detection Reagents

Several combinations of the formulation containing trehalose (Life Sciences Advanced Technologies, St. Petersburg, FL), polyethylene glycol (PEG) (Hampton Research, Aliso Viejo, CA) and dextran (Sigma-Aldrich, St. Louis, MO) were used for preservation of iSDA reagents (Table 1). The effect of the combinations of the excipients on the iSDA was first determined in a conventional tube reaction at 49° C. with MRSA genomic DNA using the thermal cycler. For lyophilization, the iSDA reagents specific to the *S. aureus* ldh1 target were mixed with the different formulation given in Table 1. The mixtures also contained the lateral flow (LF) detection twin probes, including 10 nM of biotin probe (ELITechGroup, Bothell, WA) (5'-Biotin Phosphoramidite 10-5950-95, Glen Research, Sterling, Virginia, USA), and 20 nM of capture probe (ELITechGroup, Bothell, WA). We also included a 40 nm streptavidin-coated gold (Au) detection label (Innova Biosciences, Cambridge, UK) into the iSDA reagent mix by premixing one microliter of Au label (OD 10) with 10 nM of biotin detection probe for 5 min before adding to the iSDA reagents.

TABLE 1

List of preservation mix used for dry storage and stabilization of iSDA reagents.

| | Preservation mix for dry storage (w/v) |
|---|---|
| T | 10% trehalose |
| TP | 10% trehalose |
| | 1% PEG 8000 |
| TD 70 | 10% trehalose |
| | 2.5% dextran (~70 kDa) |
| TD 500 | 10% trehalose |
| | 2.5% dextran (500 kDa) |

Standard 17 glass fiber (Std 17 GF) was laser-cut (VLS3.60, Universal Laser Systems, Scottsdale, AZ) to 20 mm×5 mm strips having a fluid capacity of 40 µl. The Std 17 GF pads were incubated in 1% bovine serum albumin (BSA) containing 0.1% Tween 20 for one hour, drained of the solution, and dried overnight at 45° C. An experimental setup for the lyophilization procedure is shown in FIGS. 9A and 9B. The BSA-coated Std 17 GF pads were placed in a sterile 12-well polystyrene plate. The outer four wells contained a neodymium magnet. An aluminum plate with neodymium magnets embedded at the four corners was placed below the 12 well-plate, serving as a thermal mass to ensure the reagent pads in the well-plate remain frozen during lyophilization. The magnets held the aluminum and well plates together FIG. 9A). About 35 µl of iSDA reagent containing Au label and the preservation mix was pipetted onto the pads. The entire apparatus, with samples loaded, was flash-frozen in liquid nitrogen, placed in a fast-freeze flask (Labconco, Kansas City, MO), and lyophilized overnight in a freeze-drying system (FreeZone 2.5 liter benchtop, Labconco, Kansas City MO) operated at a temperature of −51° C. and vacuum pressure of 0.018 mbar (FIG. 9B). After lyophilization, each pad was individually transferred to 0.5 ml sterile tubes with a hole in the cap. Sets of four tubes along with 1 gram of silica desiccant (Delta Absorbents, Roselle, IL) were placed in a moisture barrier foil pouch (Ted Pella Inc., Redding, CA) and heat-sealed. The samples were stored at 22, 35, 40, or 45° C. for 360 h or stored at 22° C. for a year.

Amplification Assay for iSDA Preservation

The Std 17 GF pads containing the dry iSDA and detection reagents stored at varying temperatures for 360 h were taken out of dry storage and placed in a Secure-Seal hybridization chamber (Electron Microscopy Sciences, Hatfield, PA), rehydrated with 33 µl of water containing the MRSA genomic DNA template (10-200 copies) and incubated at 49° C. for 30 min in the aforementioned custom oven (FIG. 9C). For long-term storage study at 22° C., the pads were periodically taken out of dry storage at 1, 2, 3, 6, and 12 months and iSDA performed with 100 copies of the genomic DNA template. After amplification, the pads were placed in a 0.2 ml tube with a hole at the bottom, which in turn was placed in a 0.5 ml tube and centrifuged to collect the amplicons and processed for lateral flow detection or gel electrophoresis.

Lateral Flow Detection of Amplicons

Lateral flow detection of iSDA amplicons was by a twin probe method co-developed with our colleagues at ELITech Group. In short, a 3'-biotinylated detection probe hybridizes to the amplicon and binds a streptavidin-coated Au nanoparticle label. A chimeric pyranosyl DNA (pDNA)-DNA capture probe hybridizes by DNA independently to the amplicon and hybridizes by pDNA to an immobilized pDNA complement. A dipstick-style LF assay format was used for demonstrating the dry preservation of the iSDA reagents. Cardboard-backed nitrocellulose FF80HP (GE Healthcare, Waukesha, WI) striped with 1) a pDNA complement linked to T20 (twenty repeats of thymidine) and 2) a T20-biotin control line (provided by ELITechGroup, Bothell, WA), and attached to a cellulose wicking pad, was cut into ~5 mm-wide strips. For detection, 28 µl of the iSDA reaction mix containing amplicons was mixed with a solution of NaCl and Triton-X100 to give final concentrations of 0.6 M and 0.8%, respectively. The mixture was added into a 96-well deep well plate (VWR, Radnor, PA) and a detection strip placed into each well for 20 minutes. The LF strips were then imaged using the procedure described below.

Lateral Flow Image Capture and Quantification

PAGE analysis was conducted under denaturing conditions. A 2.2 µl sample (from a 35 µl reaction) was mixed with 6.8 µl gel loading buffer II (Life Technologies, Carlsbad, CA) heated to 95° C. for 5 minutes, then kept on a cold block. About 7 µl of this sample mix was loaded into pre-cast 15% Novex® TBE-Urea gels (Life Technologies). A 10 bp ladder (Life Technologies) was used as a marker. Electrophoresis was conducted in an XCell SureLock™ Mini-Cell Electrophoresis System (Life Technologies) at 160 volts for ~40 minutes using a 1×TBE running buffer. The electrophoresis cell was kept in a pre-warmed water bath at 70° C. to ensure that denaturing conditions were maintained throughout. After electrophoresis, gels were stained with 2×SYBR Gold® Nucleic Acid Gel Stain (Life Technologies) in 1×TBE for 20 minutes. Stained gels were imaged using a Gel Doc™ EZ System (Bio-Rad, Hercules, CA).

Gel Electrophoresis

PAGE analysis was conducted under denaturing conditions. A 2.2 µl sample (from a 35 µl reaction) was mixed with 6.8 µl gel loading buffer II (Life Technologies, Carlsbad, CA) heated to 95° C. for 5 minutes, then kept on a cold block. About 7 µl of this sample mix was loaded into pre-cast 15% Novex® TBE-Urea gels (Life Technologies). A 10 bp ladder (Life Technologies) was used as a marker. Electrophoresis was conducted in an XCell SureLock™ Mini-Cell Electrophoresis System (Life Technologies) at 160 volts for ~40 minutes using a 1×TBE running buffer. The electrophoresis cell was kept in a pre-warmed water bath at 70° C. to ensure that denaturing conditions were maintained throughout. After electrophoresis, gels were stained with 2×SYBR Gold® Nucleic Acid Gel Stain (Life Technologies) in 1×TBE for 20 minutes. Stained gels were imaged using a Gel Doc™ EZ System (Bio-Rad, Hercules, CA).

Real-Time Fluorescence in Porous Matrix

An in-house method to monitor iSDA amplification in real time in the porous matrix was developed using a standard microplate reader (SpectraMax ID3, Molecular Device). Circular Std 17 GF pads with a fluid capacity of 13 µl were laser cut to fit the wells of a black flat-bottomed 96 well plate (Greiner Bio-One). A minor-groove-binding (MGB) fluorescent Pleiades probe, which has previously been described, was used to monitor amplification in real time. In short, the DNA probe has fluorophore and a minor groove binder at the 5' end and a quencher at the 3' end. The fluorophore is quenched in the unbound state and fluoresces when hybridized to the target amplicon. About 200 nM red-emitting Pleiades probe (ELITechGroup, Bothell, WA) was mixed to the iSDA reagents with the excipients (Table 1) and added to the Std 17 GF pads placed in a black flat-bottomed 96 well-plate and lyophilized as previously described. The samples were stored at 22 or 45° C. for 360 h and reagents were rehydrated with water containing the MRSA genomic DNA (50-1000 copies). The well-plate was sealed with a PCR plate sealer (Bio-Rad, Hercules CA) and placed in the microplate reader set at 50° C. Real-time kinetic measurement used the 593/650 nm excitation/emission setting, and fluorescence signals were acquired at 2-minute intervals.

Enzyme Activity Assay

The nicking enzyme Nt.BbvCI and WarmStart Bst polymerase 2.0 were separately lyophilized with the same formulations listed in Table 1, and tested for their activity after dry storage at different temperatures using enzyme-specific assays. The assays use reagent mixes of two components: an enzyme mix and a substrate/probe mix.

For the nicking enzyme activity assay, the 20 µL enzyme mix contained 1.6 units of Nt.BbvCI, 100 µM of each dNTPs, 50 mM potassium phosphate buffer pH 7.6, 3.75 mM magnesium sulfate, and one of the preservative mix (Table 1); and the 20 µL substrate/probe mix contained 50 mM potassium phosphate buffer, the same preservative mix, and 188 nM substrate/probe. For this assay, the substrate/probe was a DNA hairpin labeled with a quencher and a fluorophore with a minor groove binder (MGB), provided courtesy of ELITechGroup. The substrate/probe mix, always freshly prepared, and enzyme mix, either freshly prepared or extracted from pads as described below, were added to alternating rows of a 96-well microplate. The plate was loaded onto a real-time thermal cycler (CFX96, Bio-Rad Laboratories, Hercules, CA) and equilibrated to 49° C. for 10 min. Each row of enzyme mixes was combined with the adjacent row of substrate/probe mixes using a twelve-channel pipette, and then the plate was immediately read for fluorescence in the FAM channel about every 17 s for ~25 min.

For the polymerase activity assay, the 20 µL enzyme mix contained 8 units of WarmStart Bst 2.0 polymerase, 50 mM potassium phosphate buffer pH 7.6, 3.75 mM magnesium sulfate, and one of the preservative mix (Table1); and the 40 µL substrate/probe mix contained 50 mM potassium phosphate buffer pH 7.6, the same preservative mix, and 333 nM substrate, 333 µM dNTPs, 1.25 µM probes. For the polymerase activity assay, the substrate was a 90-nt, single-stranded DNA template (GCA CCG ATT TCC ACA GTT CTC CCG ACA CGC CCC TCA TAA ACA CAA TAC CAC CCA TTC ATT CCA AGC CAT ACC GAT TCC CAC AAA GCA TCT) with a 25-nt DNA primer (AGA TGC TTT GTG GGA ATC GGT ATG G), which were synthesized by Integrated DNA Technologies (Coralville, IA), and the probe was EvaGreen (Biotium). The substrate/probe mix was added to every other row of a 96-well microplate. The plate was loaded onto a real-time thermal cycler (CFX96, Bio-Rad Laboratories, Hercules, CA), and the template/primer substrate was annealed by heating to 95° C. for 2 min, then cooling to 25° C. The enzyme was then added to interstitial rows, and the plate was equilibrated to 50° C. for 10 min. Each row of enzyme mixes was combined with the adjacent row of substrate/probe mixes using a twelve-channel pipette, and then the plate was immediately read for fluorescence in the FAM channel about every 22 s for ~25 min.

Enzyme mixes were either freshly prepared or rehydrated from lyophilized Std 17 pads with water and extracted by centrifugation in a 0.45 µM filter spin column at 10,000×g for 8 min. Enzyme activities were assayed in each preservative mix (Table 1); with fresh reagents, from pads with dry reagents on the day of preparation; and from pads with dry storage at RT, 35° C., 40° C., and 45° C. after day 1 and day 15.

For the nicking activity assay, freshly prepared standard conditions used enzyme concentrations of 0×, 0.1×, 0.5×, 1.0×, and 2.0× the nominal amount of enzyme. For the polymerase activity assay, freshly prepared standard conditions used enzyme concentrations of 0×, 0.2×, 0.5×, 1.0×, and 2.0× the nominal amount of enzyme.

For analysis, a line was fit to the initial linear region of each curve while maintaining an R2 value of greater than 0.985. The slope of this fit line was plotted vs. concentration to construct a $k_{cat}$ vs. concentration calibration curve. A line was fitted to each data point in the same manner, and the slope was used to calculate the $k_{cat}$ using the calibration curve. The 100% activity was determined by the calibration curve, which uses fresh reactions in the plate. The relative activity for each condition was calculated using three technical replicates, each from 5 dried pads.

Imaging of Dried Reagents in Porous Matrix

Std 17 GF pads containing iSDA reagents, 10% trehalose and 2.5% dextran and Au label were lyophilized as previously described. The lyophilized pads were set on a flatbed scanner (Epson Perfection V700, CA USA) either dry or rehydrated with water, and scanned in 48-bit RGB mode at a resolution of 600 dpi.

For scanning electron microscopy, Std 17 GF pads with iSDA reagents containing 10% trehalose were either lyophilized or dried under vacuum using a centrifugal evaporator for 4 h (Genevac Inc, Gardiner NY). All samples were Au/Pd sputtered (SPI Module Control, Structure Probe, Inc., West Chester, PA, USA) for 103 seconds, at a ~7 nm/minute deposition rate, leaving an estimated 12 nm Au/Pd coating. A FEI Sirion scanning electron microscope with a 5 kV beam and a spot size of 3 was used for imaging.

Results and Discussion

The goal of this study was to develop a method for the long-term dry preservation of amplification reagents used in iSDA in a porous matrix that could be easily implemented in a POC NAAT platform for LRS settings. Porous materials were chosen as a matrix for drying the reagents since they are convenient to handle during drying and provided a format appropriate for integration with our 2D paper network-based POC MAD NAAT device, which has porous material connectivity for fluidic operations, and a fluorescence-based MD NAAT device (Shah et al., submitted). We included LF detection probes, and the Au-label in the iSDA reagent dry-down matrix itself, which could be applicable for an inexpensive colorimetric readout in POC device. We also used real-time fluorescence kinetics as a tool to monitor iSDA performance after dry storage. Reagents for an iSDA reaction that targeted the *S. aureus* ldh1 gene were selected for dry storage, and the limit of detection determined after rehydration.

We first tested iSDA assay compatibility with a variety of porous matrices. After the selection of a porous matrix, we tested a suitable drying and storage method. We then tested the stability of dry iSDA reagents, including the detection labels, in various preservation formulations by performing amplification in the porous matrix itself, followed by dip-stick-style LF detection and gel electrophoresis. We also used a real-time fluorescence measurement in the porous matrix to assess the iSDA reagent stability. Furthermore, we separately tested the stability of the two enzymes (nicking enzyme and the polymerase) in dry storage in the porous matrix by using enzyme-specific activity assays. A range of temperatures of storage (22-45° C.) was studied for applicability to LRS, especially in hot climates where the ambient temperatures can be in the 40-45° C. range.

Porous Matrix Selection for iSDA Assay

Figure 1A:
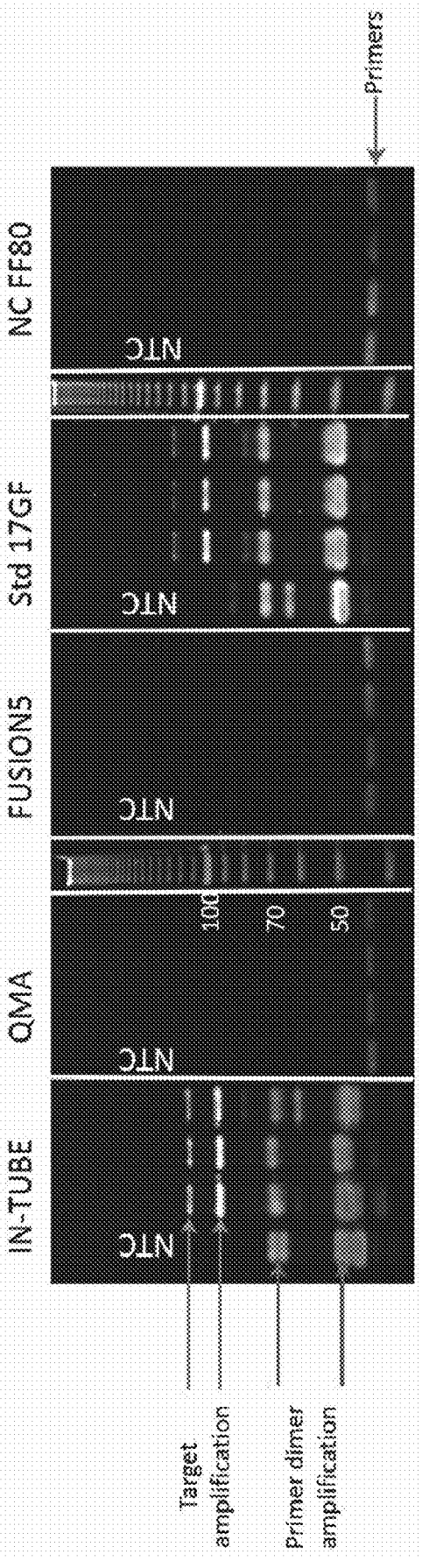
FIG. 1A provides denaturing PAGE image showing products of the ldh1 iSDA assay in a few selected porous materials, according to an embodiment of the present disclosure. Std 17 GF showed the targeted amplification product bands at ~100 and 120 nucleotides (green arrow) comparable to the assay as performed in-tube (conventional polypropylene tube). Primer dimer side products are indicated with an arrow. Quartz (QMA), nitrocellulose (NC-FF80), and Fusion 5 totally inhibited amplification, including the primer-dimer side reactions.
Figure 1B:
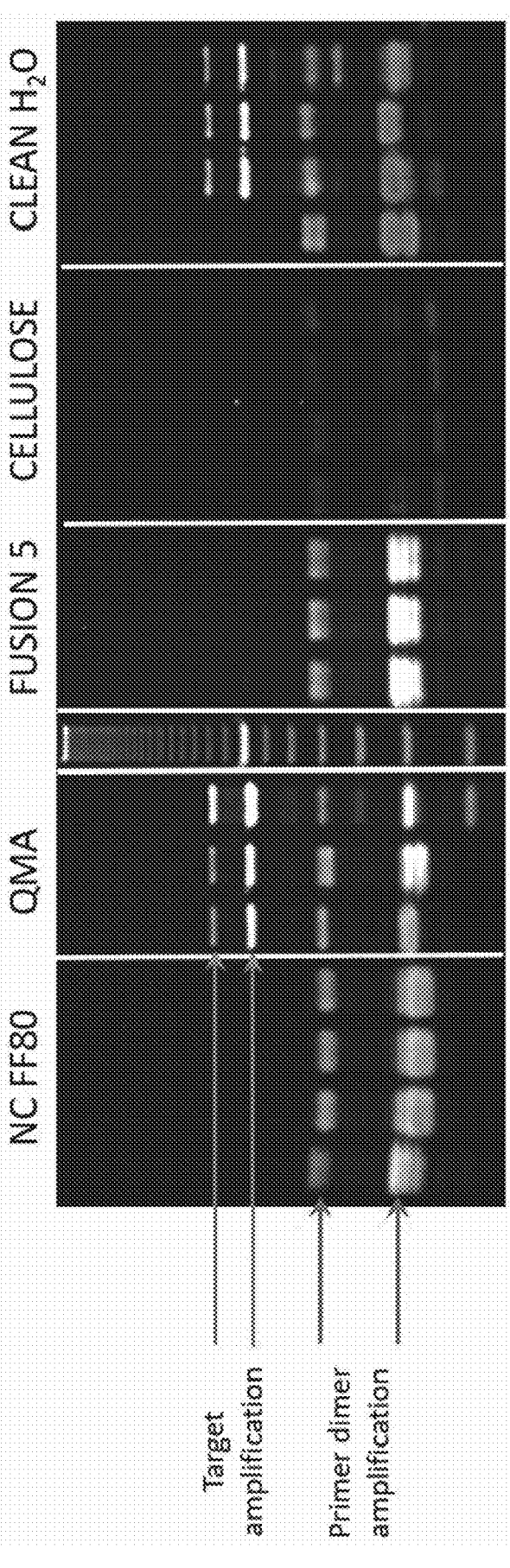
FIG. 1B provides a gel image showing the effect of leachate from porous materials on iSDA as performed in a tube, according to an embodiment of the present disclosure. Leachate from NC-FF80, Fusion 5, and cellulose significantly inhibited iSDA as seen by very faint product-specific products, whereas the leachate from QMA did not affect the iSDA assay, according to embodiments of the present disclosure.

To select porous matrices that are compatible with iSDA, we first added the iSDA reagents directly to the native porous materials without any pre-treatment. We used a variety of porous matrices, including nitrocellulose (FF80), cellulose (CF5), quartz (QMA), Fusion 5, and Std 17 GF, and tested for the ldh1 iSDA with 100 MRSA genomic copies in a custom oven. We found that, of this set, only Std 17 GF supported iSDA, and had sensitivity comparable to in-tube assay, as seen by gel electrophoresis (FIG. 1A). The target amplification products (100 and 120 bp) and the primer-dimer side products, as seen on the gel, are an indication of a successful iSDA. The other materials (nitro-cellulose, cellulose, Fusion 5, and quartz) inhibited iSDA, as neither the ldh1-specific products nor the inevitable primer-dimer side products could be seen on the gel. We speculated two reasons for the failure of amplification in these mate-rials; 1) that the materials had assay inhibiting compounds, or 2) the interaction of the enzymes with the surface of the materials rendered them inactive. To investigate the failure of amplification with those matrices, we tested the leachate from incubation of these materials in water in an in-tube iSDA with 100 MRSA genomic copies. We found that the leachate from the nitrocellulose, cellulose, and Fusion 5 significantly inhibited the assay, as seen by the very faint product-specific bands, compared to the strong control bands in the condition with clean water (FIG. 1B). Interest-ingly, for the quartz material, the leachate did not inhibit iSDA in the in-tube assay (FIG. 1B) compared to the in-material testing in FIG. 1A, possibly indicating that the surface of the quartz material inactivated or immobilized some or all of the reagents. These porous materials could support iSDA after washing away the inhibitors and/or blocking surfaces with protein coating, although we did not pursue these efforts. We used Std 17 GF as our material of choice for all the reagent dry storage studies.

Dry Storage of iSDA Reagents

Figure 2:
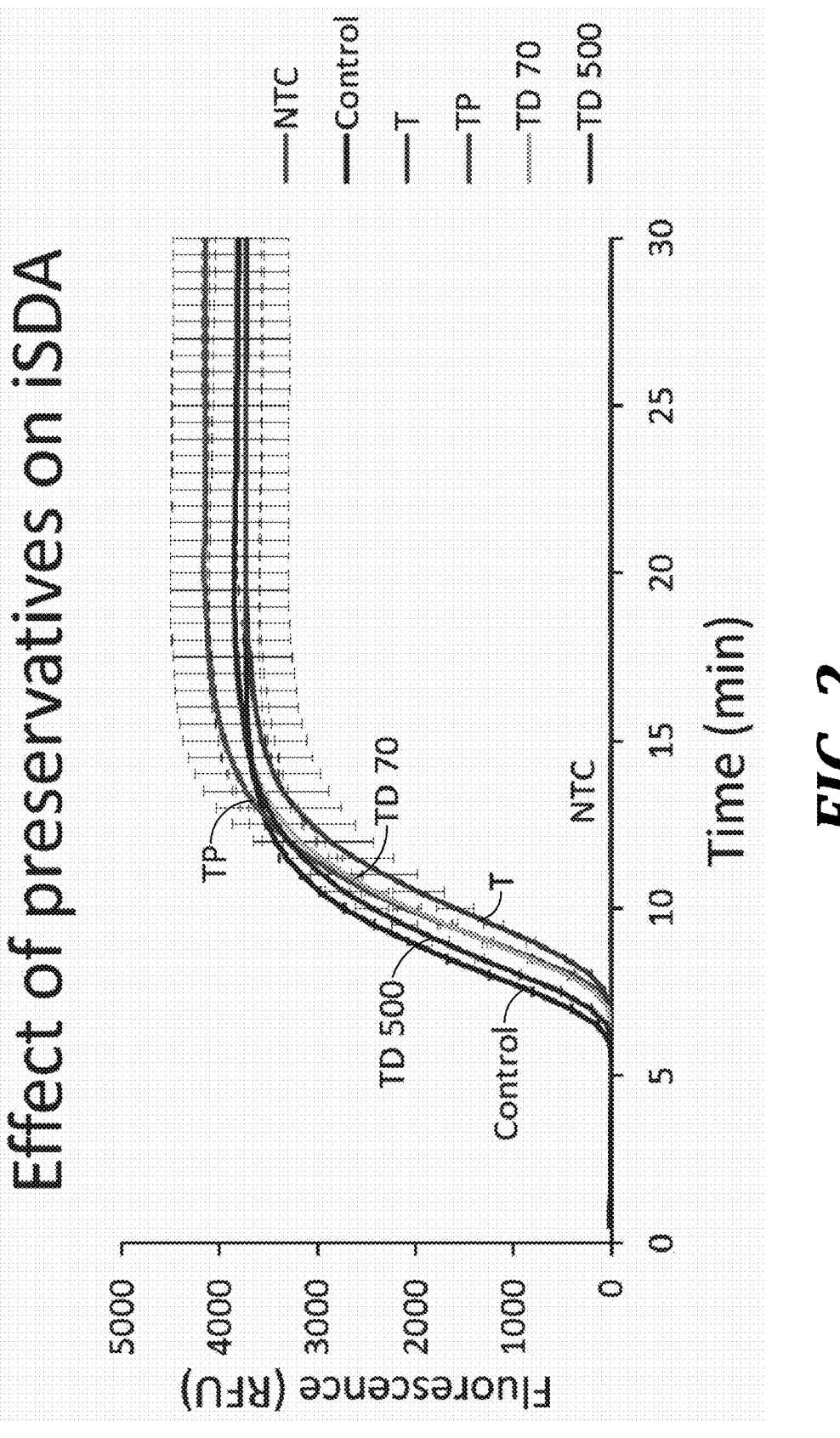
FIG. 2 illustrates the effect of combinations of preservatives on ldh1 iSDA with 250 copies of MRSA genomic DNA measured by real-time fluorescence using the target-specific probe, according to an embodiment of the present disclosure. The control sample was without any preservatives. Curves are mean of 3 replicates, and error bars are standard deviation. The preservatives did not have any negative effect on iSDA. The lift-off times of the reactions were nearly identical (~7 min), and the peak fluorescence levels were similar for all the formulations. (T=10% trehalose, TP=10% trehalose+1% PEG, TD70=10% trehalose+2.5% dextran (~70 kDa), TD500=10% trehalose+2.5% dextran (500 kDa) and NTC was a no-template control).

Several formulations of preservatives involving combi-nations of trehalose, PEG, and dextrans (Table 1) were considered for stabilizing the iSDA reagents for dry storage. It was assumed that the most unstable components of the amplification "master mix" would be the proteins: the nick-ing enzyme and the polymerase. The preservative formulations were initially tested for any adverse effect on iSDA by real-time amplification using a red-emitting fluorescent tar-get-specific MGB probe in an in-tube assay with fresh reagents. The lift-off time of the reaction and the fluores-cence levels serve as an indication of the performance of iSDA. In the literature, PEG and dextran have been reported to act as crowding agents that enhance loop-mediated iso-thermal amplification (LAMP) and also to provide protein stabilization by volume exclusion. We found that neither trehalose alone, nor in combination with moderate concen-trations of the polymers, dextran and PEG, had any negative effect on iSDA when tested at 250 input copies of MRSA genomic DNA (FIG. 2). The lift-off time of the reaction (~7 minutes) and the fluorescence levels were comparable to the control sample without preservatives.

Next, we developed a freeze-drying method to store all the iSDA reagents in a Std 17 GF porous matrix. In addition, we were able to include the target-specific detection probes and the streptavidin-coated Au label into the iSDA reagent mix itself. The iSDA reagents, the detection probes, and the Au label in various preservation formulations (Table 1) were lyophilized in 5 mm×20 mm Std 17 GF pads and stored at a range of temperatures (22-45° C.) for 360 hours. The pads were rehydrated, and iSDA assay performed within the matrix with 100 copies of MRSA genomic DNA followed by dip-stick style LF detection. The lateral flow detection of the iSDA amplicons was by a twin probe method co-developed with our colleagues at ELITech Group and previously pub-lished. In this present disclosure, Au labels, instead of the blue latex beads, were used for colorimetric detection. In this LF detection method, the twin probes hybridize with the amplicon and are captured by the test line via the comple-mentary pDNA on the nitrocellulose. Any free probe will flow downstream and bind to a biotin control line via streptavidin on the Au label.

Figure 3A:
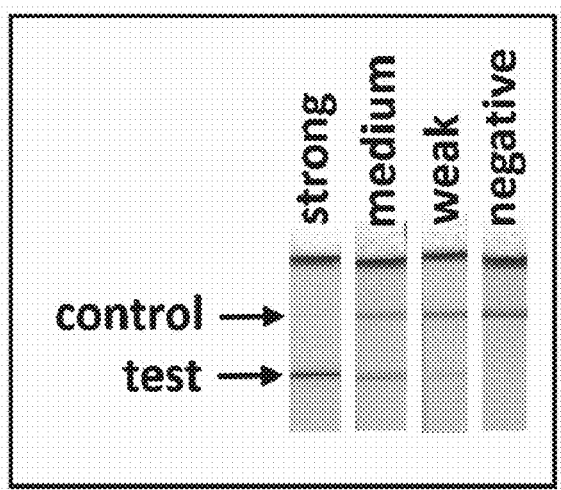
FIGS. 3A-3C illustrate performance of ldh1 iSDA of reagents stored dry in Std 17 GF for 360 h with different preservative formulations (Table1), and range of temperatures, according to an embodiment of the present disclosure.

An example of an LF detection strip with either a strong, medium, weak or negative amplification signal at the test line for the dry storage conditions with 100 genomic copy numbers is shown in FIG. 3A. Under the condition of the biotin probe and the streptavidin-Au label concentrations we used, a robust amplification gave us an intense test line signal with a very weak control line, and a negative ampli-fication showed only an intense control line. Based on the stability of the iSDA reagents in different dry storage con-ditions, we saw a range of varying intensities for the test and the control line in an inverse relationship.

Figure 3B:
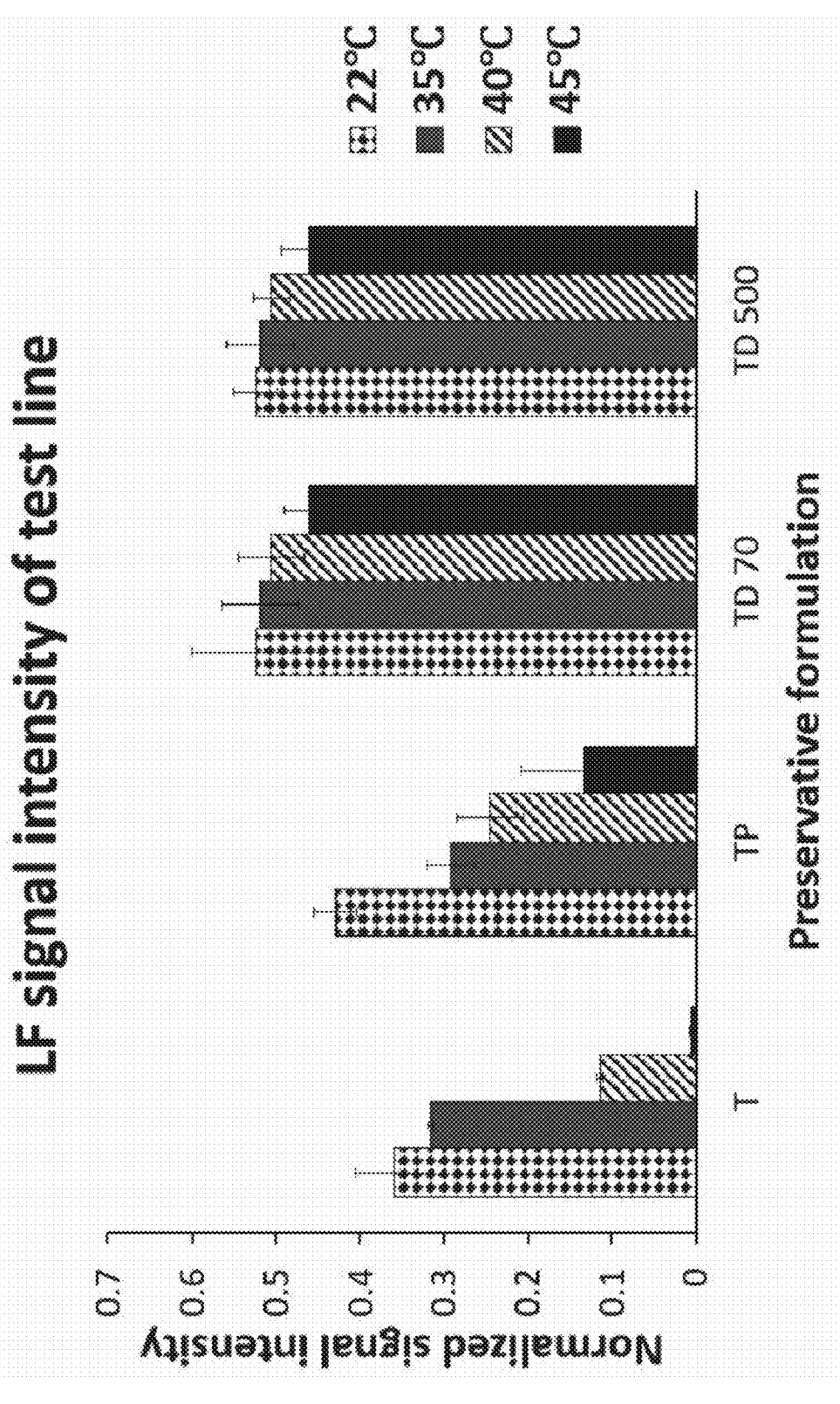
Figure 3C:
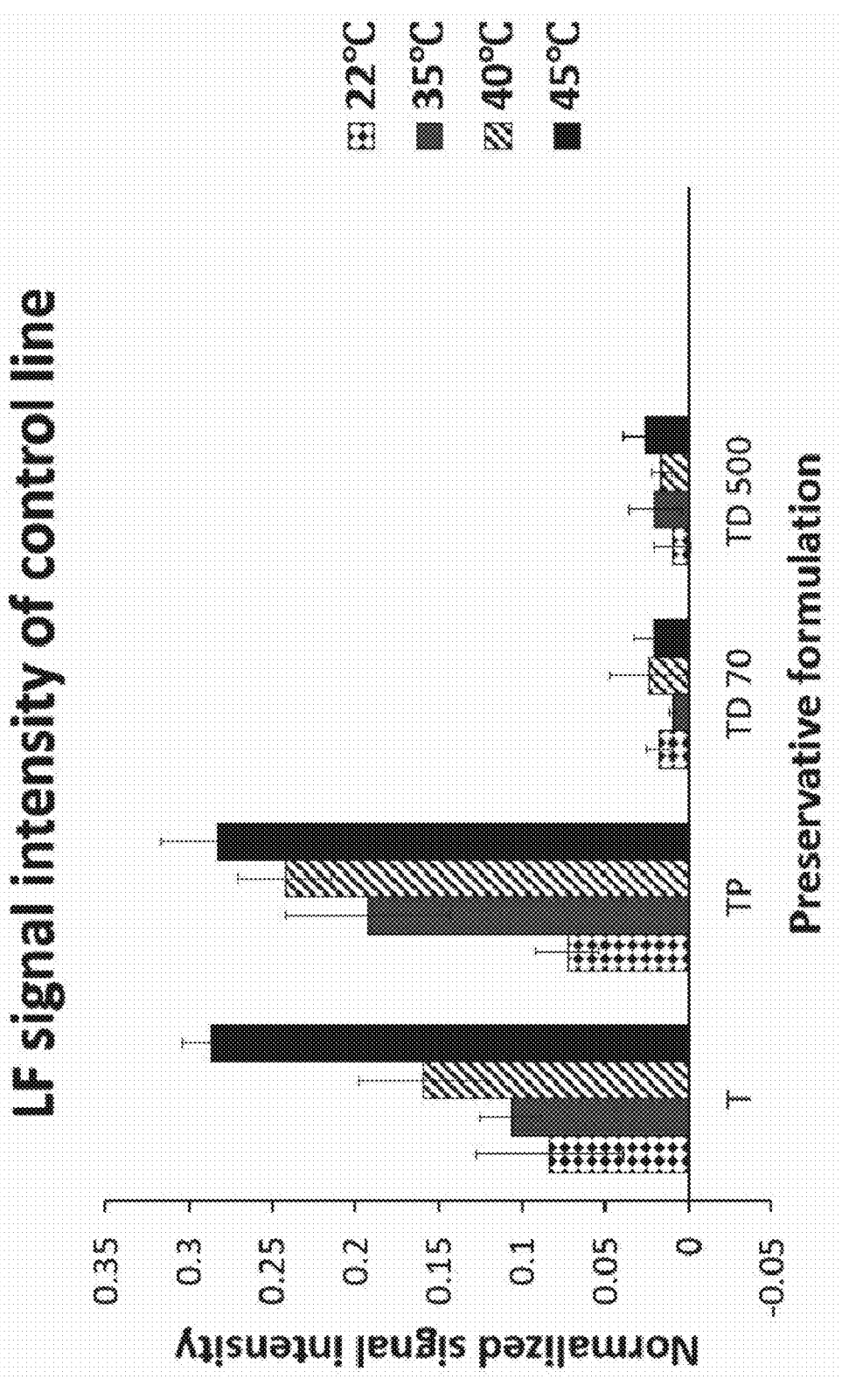

The signal intensities for the test and control line were measured for all conditions of dry storage (FIGS. 3B and 3C). For formulations in which both trehalose and dextran were included, excellent stability was achieved at all tem-peratures of storage, including 45° C., as indicated by strong signal intensities of the test line and a very weak control line. The test line signal intensity was comparable to iSDA with a fresh reagent for the 100 genomic copy number (FIG. 10). With trehalose alone, target amplification failed for storage at 45° C., and amplification was weaker for 22, 35, and 40° C. (when compared to samples with trehalose and dextran) as indicated by weaker signal intensity for the test line and stronger intensity for the control lines. Samples with both trehalose and PEG performed only slightly better than trehalose. This inverse relationship of the control and test line intensities served as a qualitative measure for screening for iSDA reagent stability under different storage conditions. A similar relationship was seen when a LOD for ldh1 iSDA using fresh reagents was performed with varying genomic copy numbers (FIG. 10B). At lower copy numbers, the signal intensity of the control line is stronger than the test line, and vice versa with increasing copy number. While the method for LF detection is very robust and sensitive, it gives us only a qualitative measure of reagent stability. Testing the stability of the reagents with real-time kinetics in terms of lift-off time and fluorescence levels gave us more quantitative results without the influence of excipients in lateral flow detection.

Figure 4A:
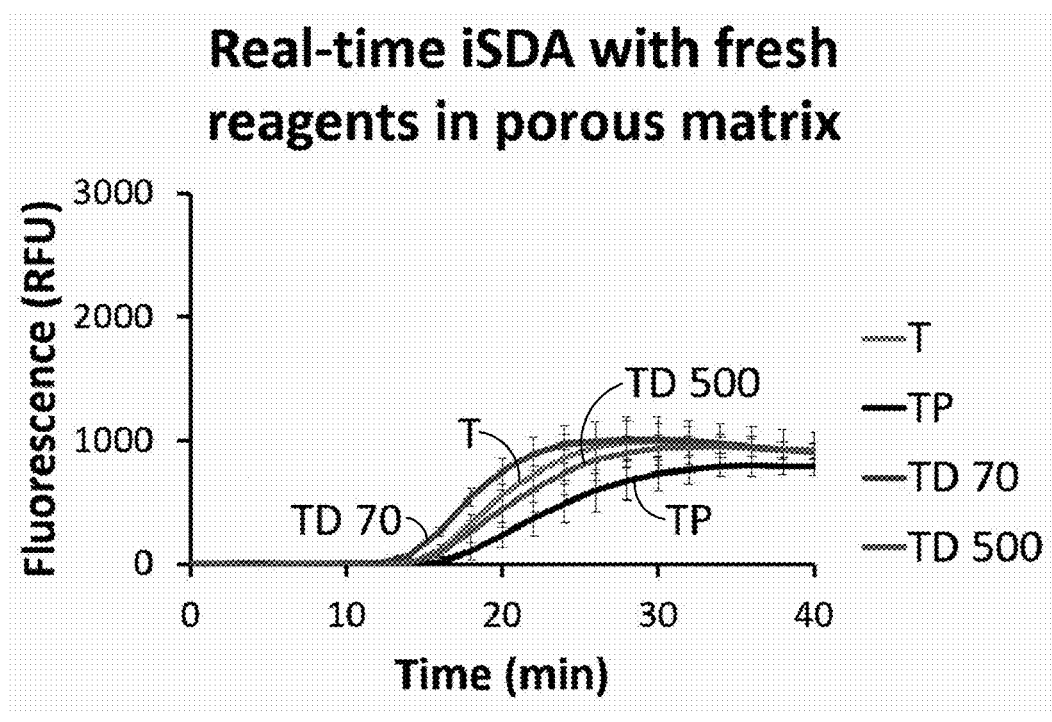
Figure 4B:
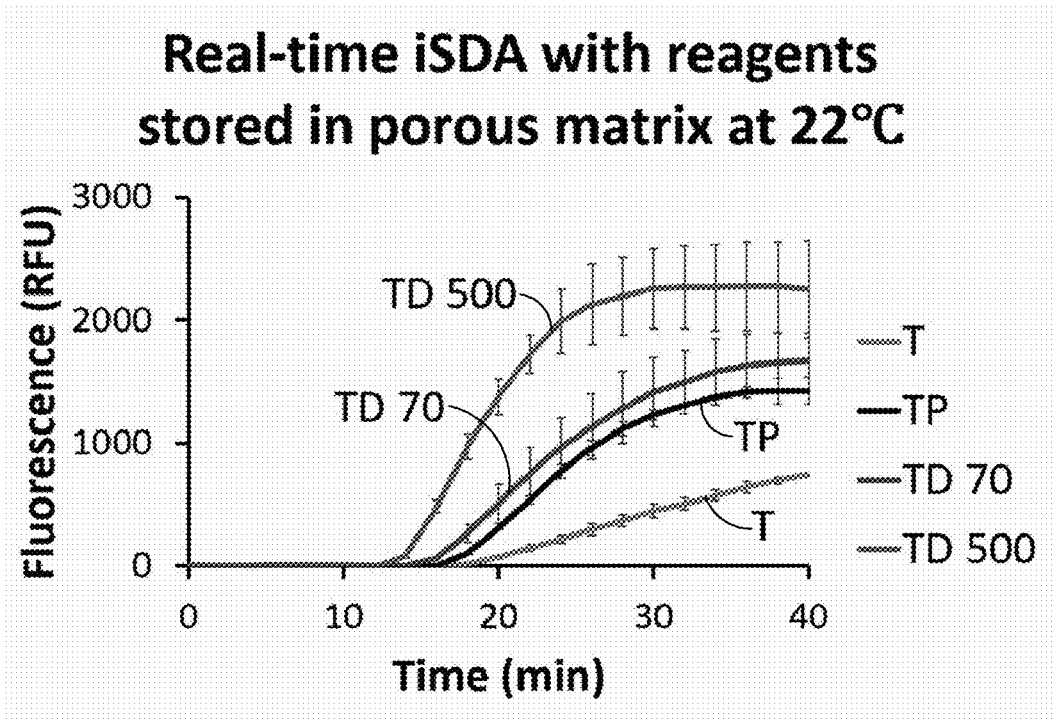
Figure 4C:
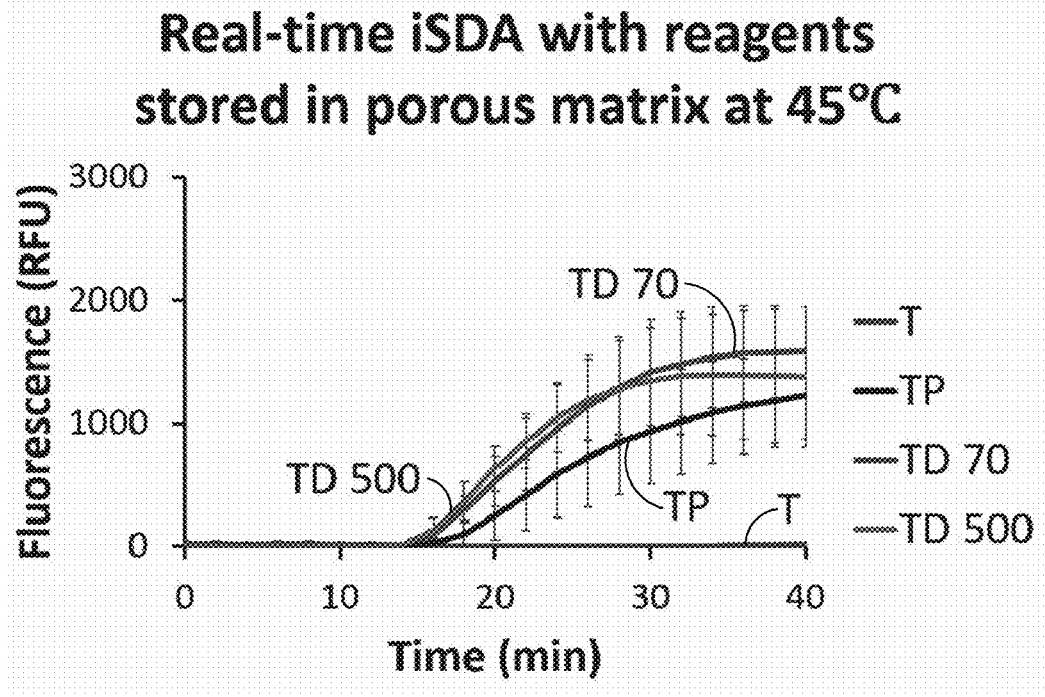

We included a target-specific red-emitting fluorescent probe instead of LF probes to monitor iSDA in real time after rehydration in the porous matrix using a plate reader to compare the performance of different formulations at 22° C. and 45° C. storage. We found that the lift-off time of the iSDA assay for almost all conditions was within 15-18 minutes and comparable to fresh reagents in the porous matrix using 250 copies of MRSA genomic DNA (FIGS. 4A-4C).

The peak fluorescence levels, however, varied for different formulations with the highest signal for formulations with trehalose and dextran. The trehalose only formulation did not amplify at 45° C. storage and performed poorly at 22° C. Our results with fluorescence measurement directly matched the LF detection data presented in FIGS. 3A-3C for the formulations used for dry storage of iSDA reagents.

Interestingly, the peak fluorescence levels for dry stored conditions, especially for TP TD 70 and TD 500 (FIGS. 4B and 4C), were higher than for iSDA with fresh reagents (FIG. 4A) in the porous matrix. We believe that this is due to non-uniform rehydration of reagents in the porous matrix, causing a concentration gradient. As a result, some areas in the matrix might have had robust amplification resulting in higher fluorescence measured locally, compared to the fresh reagents which are homogenous throughout the matrix. The result also agrees with additional unpublished data which suggests that the iSDA reaction is tolerant of a wide concentration range (0.5×-2.5×fold). While we do not get the spatial information of the amplification using the plate reader, support for this hypothesis has been addressed by fluorescence imaging in a submitted publication (Shah et al.).

Based on these results, we conclude that the addition of dextran to trehalose preserved the iSDA reagents better than other formulations at elevated temperatures in the Std 17 GF. In the literature, dextran has been reported to provide protein stability during freeze-drying.

Rehydration-Profile of Dry-Stored Preservative Mixtures in Porous Matrix

Mock reagent samples containing different combinations of preservation formulation with Au label as a visual marker were prepared; i) no sugar, ii) 5% trehalose, iii) 10% trehalose, iv) 10% trehalose and 2.5% PEG, v) 10% trehalose and ~70 kD dextran and vi) 10% trehalose and 500 kD dextran. About 35 μl of the mock sample containing 4 μl of Au label, OD 10 (Innova Biosciences, Cambridge, UK) was added to 5×20 mm BSA coated Std17 GF pads and lyophilized as described above. The dry pads were then laid on a flatbed scanner. A piece of fresh 5×5 mm Std 17 GF pad was placed overlapping the lyophilized pads. The pads were rehydrated by slowly adding water to the fresh GF pad until the fluid front reached the end of the lyophilized pad. A white laminate card was placed over the pads and imaged as described below. For calibration, wet reagents containing a range of fold-concentration (0.25×-4×) of Au label where, 1×=4 μl of OD 10 Au label, was added on to Std 17 GF pads and imaged similarly. For generating rehydration profiles, the pads were imaged on the scanner in 48-bit RGB mode (16-bit per color channel) at a resolution of 600 dpi. For analysis, signal intensities from the green channel were used. A plot profile across the length of the pad was generated by averaging intensities along successive widths using ImageJ (NIH). The signal intensities from the plot profiles were converted to gold concentration using a calibration plot. To generate a calibration plot, wet GF pads containing different concentration of the gold label were similarly imaged on the flatbed scanner, and mean green-channel intensities over the entire pads were calculated.

A two-tailed Student's t-test was used for statistical comparisons of rehydration profile between various preservation formulations. For this, the ratio (R) of amount of Au label present in the downstream and upstream half of each pad was calculated and compared between different preservation formulations.

Reagents contained 50 mM potassium phosphate buffer pH 7.6, 3.8 mM magnesium sulfate, 100 μM of each dNTP, 250 nM extension primer E1, 500 nM extension primer E2, 50 nM each of bumper primers B1 and B2, 8 units of WarmStart Bst 2.0 polymerase (New England Biolabs, Ipswich, MA) and 1.6 units of nicking enzyme Nt.BbvCI (New England Biolabs, Ipswich, MA).

The mixtures also contained the lateral flow (LF) detection twin probes, including 10 nM of biotin probe (ELITech-Group, Bothell, WA) (5'-Biotin Phosphoramidite 10-5950-95, Glen Research, Sterling, Virginia, USA), and 20 nM of capture probe (ELITechGroup, Bothell, WA).

Au label and probes were added after amplification for the FIG. 8d.

Rehydration-Profile of Different Preservation Formulations in Std 17 Gf

In our study, we chose a rectangular piece of matrix in which to store the iSDA dry reagent; such a piece of reagent-filled Std 17 GF has been incorporated into the 2DPN NAAT device. It was important to understand the iSDA reagent distribution along the length of the pad during rehydration. Different preservation formulations containing trehalose, PEG and dextran, along with Au label as a visual marker were lyophilized in Std 17 GF pads, rehydrated by introducing fluid from one end, and intensity plots were generated along the length of the reagent pads. A fold-concentration to intensity calibration curve was first generated using varying fold concentration of the Au label (FIG. 8A). Using this calibration curve, the intensity profiles were converted to fold-concentrations of the Au label. The rehydration profile-plots in FIG. 8B indicate that, for samples without sugar or only trehalose, the Au label was compacted into the last-wetted portion of the pad, whereas addition of PEG or dextran resulted in more uniform distribution across the length of the pad. We believe the samples with PEG or dextran result in slower dissolution in the porous matrix due to higher viscosity compared to trehalose alone.

We further calculated the ratio (R) of Au label between downstream and upstream half of the pad for each formulation (FIG. 8C). A two-tailed Student's t-test used for statistical comparisons of the ratios between various preservation formulations indicated that addition of either PEG or dextran to trehalose resulted in a more uniform Au label distribution (P>0.05). Also, addition of dextran 500 to trehalose was significantly better than PEG (P>0.05).

Based on the results of the rehydration profile, we would expect iSDA reagents to be distributed within similar range of concentrations (0.5×-2.5×) during rehydration. We therefore tested the tolerance of the iSDA to different fold-concentration of the reagents in a tube assay. Au label and probes were added after amplification. The assay was found to be quite tolerant to a wide range of reagent concentrations (0.5×-2.5×) as seen by LF detection (FIG. 8D). We would expect a similar response of iSDA within the rehydrated pad in that range of reagent concentrations.

Enzyme Activity

Another way to address the performance of iSDA at different storage conditions is to assess the stability of the two enzymes individually because they are likely the components of the amplification mixture most vulnerable to degradation. We, therefore, stored the nicking and the polymerase enzymes separately in Std 17 GF porous matrix under the same dry storage conditions as the iSDA reagents and used enzyme-specific assays to test the stability.

The results of the enzyme activity assays are shown in FIGS. 5A and 5B. The activity of polymerase does not appear to decrease appreciably over storage temperatures for all formulations except trehalose+PEG. The activity of the nicking enzyme does appear to decrease significantly over time at elevated temperatures. PEG was observed to be an overall detriment to storage for enzymes. The preservation of polymerase activity at 45° C. over time was expected as the optimal working temperature for the enzyme is listed as 65° C. Loss of nicking enzyme activity during storage at 45° C. appears the likely candidate for the decrease of performance of iSDA over time. The decrease in activity at the elevated temperature over time of nicking enzyme was expected because the reported optimal temperature of the enzyme is 37° C.

Limit of Detection with Dry Stored iSDA Reagents

Next, the limit of detection (LOD) for the iSDA reagents stored dry in Std 17 GF at 22° C. and 45° C. for 360 h with various formulations was determined by LF detection. From the LOD with fresh iSDA reagents (FIG. 10A), we determined that the linear range of the normalized signal intensity of the test line was below 100 copies. We, therefore, tested the ldh1 iSDA performance in the range of 10-200 genomic copies for all the formulations stored at 22° C. and 45° C. The normalized test line signal intensities for varying copy numbers are given in FIGS. 6A and 6B. We found that the samples stored in the presence of both trehalose and dextran showed excellent stability down to 10 copies of genomic DNA for both at 22° C. and 45° C. and comparable to fresh reagents (FIG. 10A). For samples with trehalose only, or with trehalose and PEG, the test line signal intensities were lower below 50 genomic copies at 22° C. storage compared to TD 70 and TD 500 (FIG. 6a), and near zero for samples stored at 45° C. indicating poor stability (FIG. 6b).

We also tested the LOD for the ldh1 iSDA by real-time fluorescence for the reagents stored in Std 17 GF with both trehalose and dextran (TD 500) at 22° C. and 45° C. for 360 h. We found that the lift-off time for all copy numbers (50-1000) was ~15 mins (FIGS. 11A and 11B). The fluorescence peak intensities were a little higher for samples stored at 22° C. than 45° C. indicating slightly lower amplification efficiency at the higher storage temperature.

Long-Term Stability of iSDA Reagents

To study the long-term stability in dry storage, the iSDA reagent mix and the Au label with 10% trehalose and 2.5% dextran (~70 kDa) were stored in Std 17 GF at room temperature (~22° C.) for one year. They were periodically tested by performing iSDA assay within the porous matrix with 100 copies of MRSA genomic DNA, and the amplicons detected by LF and gel electrophoresis. We found excellent stability of the iSDA reagents after one year of dry storage by LF detection and by gel electrophoresis (FIG. 7). The test line signal intensities on the LF strips were comparable to those with fresh reagents.

FIGS. 7A-7C demonstrate long-term iSDA reagent stability in the Std 17 GF, according to embodiments of the present disclosure. FIG. 7A illustrates normalized intensity of the LF test line after dry storage at 22° C. at different times. FIG. 7B includes images of lateral flow detection strips at various time points. "C" indicates the control line, and "T" is the test line for ldh1 assay on the detection strips. FIG. 7C includes corresponding gel images of the ldh1 amplicon products (indicated by arrow) at various time points. NTC is no template control. The iSDA reagents in the presence of 10% trehalose and 2.5% dextran performed well after 12 months of dry storage, with signal intensities similar to that observed with fresh reagents.

Our method of dry storage of isothermal amplification reagents in the porous matrix has several useful features. First, reagents stored in a glass fiber pad can be easily implemented for several applications with porous material fluid connectivity, especially in paper-based POC integrated systems. An image of the Std 17 GF pad with iSDA reagents lyophilized in the presence of 10% trehalose and 2.5% dextran before and after rehydration is shown in FIG. 12A. The glass fiber provides physical support during lyophilization, allowing passive spreading of the reagents across the matrix that allows rehydration and amplification function without excessive variation in reagent concentration throughout the volume of the pad. We also compared scanning electron micrographs of reagents dried in Std 17 GF in the presence of 10% trehalose, either by vacuum drying or by lyophilization. In the lyophilized sample, the reagents migrate to the small features of the Std 17 GF and appear as dry sheets stretched across the void with high surface-area-to-volume ratio compared to the vacuum dried samples, were reagents appear as large clumps (FIG. 12B). Differences in freezing rate, handling time, vacuum, and time-temperature profiles could all contribute to the differential distribution of the reagents once dry. These two different drying conditions could be expected to perform differently in both how well reagents are preserved, along with how the dry structures enable imbibition and eventual dissolution once wet. We observed differences in wetting: the lyophilized pads tended to wet faster and more uniformly than the vacuum-dried pads (data not shown).

Second, we included all the detection reagents, including LF probes and Au label, with the amplification reagents mix for dry storage. This is an advantage when implemented in an inexpensive POC device with colorimetric LF readout, as it alleviates the need to store the detection label separately, and the complexity necessitated by subsequent rehydration and mixing detection chemistry with the amplicon.

Third, we were also able to include the target-specific fluorescent probe in the dry pads in our study: this facilitates real-time fluorescence imaging of amplification using mobile phone in POC integrated systems (Shah et al.). One potential disadvantage of our method is that scale-up requires creation of a specialized production facility for a specialized lyophilization procedure for the dry pads.

This method of dry storage of iSDA reagents along with the LF detection probes in the same mix has been incorporated into a sample-to-result instrument-free MAD NAAT device for the detection of MRSA from nasal swabs. A modification of this device with a USB-powered printed circuit board, the MD NAAT device, with dry reagents including fluorescence detection with mobile phone imaging has been described in a submitted publication (Shah et al.). Our future publications will describe our progress in adapting this dry-down method to include reverse transcriptase for isothermal amplification methods for detection of RNA viruses such as SARS-CoV-2.

CONCLUSIONS

We developed a method for dry preservation of all reagents necessary for iSDA amplification and detection of DNA targets in a porous matrix. The reagents also included either fluorescence probes or Au-label probes for detection, thus eliminating the need to store them separately. We showed that the iSDA reagents retained a high level of activity after dry storage in a glass fiber matrix with trehalose and dextran at temperatures up to 45° C. Lateral flow readout of iSDA produced consistently detectable colorimetric signals at 10 copies or above (visual readout by eye or by scanner), while fluorescence readout was reliably measurable at 50 copies or greater (fluorescence measurement in a plate reader). We demonstrated long-term stability of reagents up to one year at 22° C. Our method for drying the reagents onto a glass fiber pad has the benefit of easy incorporation into POC devices, including conventional microfluidic or paper-based devices, especially in places where the ambient temperatures are in the 40-45° C. range. Further, we have demonstrated iSDA in a fully integrated 2DPN MAD NAAT device with dry reagents and successfully validated with real patient samples. Dry preservation of amplification reagents in porous matrices could be used for a variety of applications and has particular advantages for use in POC devices with LF detection or real-time fluorescence readout, portability, and ease-of-use in low resource settings.

While illustrative embodiments have been illustrated and described, it will be appreciated that various changes can be made therein without departing from the spirit and scope of the invention.

The embodiments of the invention in which an exclusive property of privilege is claimed are defined as follows:

1. A fluidic device comprising:
   a fibrous pad configured to transport liquid therethrough by capillary action; and
   a lyophilized reagent depot configured to support nucleic amplification of a target nucleic acid molecule to produce amplicons when dissolved, wherein the lyophilized reagent depot is disposed on the fibrous pad, the lyophilized reagent depot comprising:
   a nucleic acid amplification enzyme configured to perform a nucleic acid amplification reaction producing amplicons;
   a lyophilization agent; and
   a lateral flow strip positioned to receive the liquid from the fibrous pad and configured to produce a detectable signal in response to contact with a target nucleic acid molecule and/or an amplicon thereof.

2. The fluidic device of claim 1, wherein the lyophilization agent comprises a saccharide or a polyethylene oxide.

3. The fluidic device of claim 1, wherein the lyophilization agent comprises trehalose, dextran, polyethylene glycol (PEG), and combinations thereof.

4. The fluidic device of claim 1, wherein the lyophilization agent comprises trehalose and dextran.

5. The fluidic device of claim 4, wherein the dextran has a weight average molecular weight in a range of about 70 kDa to about 500 kDa.

6. The fluidic device of claim 1, wherein the nucleic acid amplification enzyme is a polymerase.

7. The fluidic device of claim 1, wherein the lyophilized reagent depot further comprises a nicking enzyme.

8. The fluidic device of claim 1, wherein the lyophilized reagent depot further comprises extension primers and bumper primers configured to amplify the target nucleic acid molecule.

9. The fluidic device of claim 1, wherein the lyophilized reagent depot further comprises a reverse transcriptase.

---

SEQUENCE LISTING

<160> NUMBER OF SEQ ID NOS: 2

<210> SEQ ID NO 1
<211> LENGTH: 90
<212> TYPE: DNA
<213> ORGANISM: Artificial sequence
<220> FEATURE:
<223> OTHER INFORMATION: Synthetic

<400> SEQUENCE: 1
gcaccgattt ccacagttct cccgacacgc ccctcataaa cacaatacca cccattcatt      60
ccaagccata ccgattccca caaagcatct      90

<210> SEQ ID NO 2
<211> LENGTH: 25
<212> TYPE: DNA
<213> ORGANISM: Artificial sequence
<220> FEATURE:
<223> OTHER INFORMATION: Synthetic

<400> SEQUENCE: 2
agatgctttg tgggaatcgg tatgg      25

10. The fluidic device of claim 1, wherein the lyophilized reagent depot further comprises detection reagents configured to hybridize with the amplicons.

11. The fluidic device of claim 10, wherein the detection reagents comprise biotinylated detection probes configured to hybridize with the amplicons and streptavidin-coated gold nanoparticles.

12. The fluidic device of claim 10, wherein the detection reagents comprise a fluorophore, and wherein the fibrous pad further comprises a detection zone comprising a quencher configured to quench fluorescence of the fluorophore.

13. The fluidic device of claim 1, wherein the fibrous pad comprises a material selected from the group consisting of nitrocellulose, cellulose, quartz, glass fiber, and combinations thereof.

14. The fluidic device of claim 1, wherein the fibrous pad comprises glass fiber.

15. The fluidic device of claim 1, wherein the fibrous pad comprises a fibrous pad that has been washed of leachates before introducing the lyophilized reagent depot.

16. A method of preparing a fibrous pad comprising dried reagents deposited thereon, the method comprising:

depositing a reagent solution on a fibrous pad configured to transport liquid therethrough by capillary action, wherein a lateral flow strip is positioned to receive the liquid from the fibrous pad and configured to produce a detectable signal in response to contact with a target nucleic acid molecule and/or an amplicon thereof, the reagent solution comprising:

a nucleic acid amplification enzyme configured to perform a nucleic acid amplification reaction producing amplicons; and a lyophilization agent; and lyophilizing the reagent solution to provide a lyophilized reagent depot on the fibrous pad.

17. The method of claim 16, wherein the lyophilization agent comprises trehalose, dextran, polyethylene glycol (PEG), and combinations thereof.

18. The method of claim 16, wherein the lyophilization agent comprises trehalose and dextran.

19. The method of claim 18, wherein the reagent solution comprises trehalose in a concentration of about 5% w/v to about 15% w/v and dextran in a concentration of about 1% w/v to about 5% w/v.

20. The method of claim 16, wherein the fibrous pad comprises glass fiber.

21. The method of claim 16, further comprising washing the fibrous pad to remove leachate from the fibrous pad before depositing the reagent solution on the fibrous pad.

22. The method of claim 16, wherein the reagent solution comprises magnesium sulfate in a concentration of in a range of about 15 mM and about 150 mM.

23. The method of claim 16, wherein the reagent solution comprises potassium phosphate in a concentration of in a range of about 1 mM and about 15 mM.

* * * * *